United States Patent
Fisher et al.

(10) Patent No.: US 9,468,753 B2
(45) Date of Patent: Oct. 18, 2016

(54) SYSTEM AND METHOD FOR STIMULATING MOTOR UNITS

(71) Applicant: Case Western Reserve University, Cleveland, OH (US)

(72) Inventors: Lee Fisher, Pittsburg, OH (US); Ronald Triolo, Cleveland Heights, OH (US); Dustin J. Tyler, Highland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 101 days.

(21) Appl. No.: 13/918,440

(22) Filed: Jun. 14, 2013

(65) Prior Publication Data
US 2014/0031910 A1    Jan. 30, 2014

Related U.S. Application Data

(60) Provisional application No. 61/659,508, filed on Jun. 14, 2012.

(51) Int. Cl.
*A61N 1/05* (2006.01)
*A61N 1/36* (2006.01)

(52) U.S. Cl.
CPC .......... *A61N 1/0556* (2013.01); *A61N 1/36003* (2013.01)

(58) Field of Classification Search
CPC ..................... A61N 1/36003; A61N 1/0556
USPC ............................... 607/118, 48, 49
See application file for complete search history.

(56) References Cited

U.S. PATENT DOCUMENTS

2011/0093036 A1* 4/2011 Mashiach ............... 607/48
2011/0112605 A1* 5/2011 Fahey ..................... 607/48

* cited by examiner

*Primary Examiner* — Alyssa M Alter
(74) *Attorney, Agent, or Firm* — Tarolli, Sundheim, Covell & Tummino LLP

(57) ABSTRACT

Systems and methods are provided for stimulating motor units. An electrode array includes a plurality of electrodes configured to provide stimulation to respective motor units of a plurality of independent, mutually agonist motor units. A stimulator assembly is configured to provide a stimulation current to each electrode of the plurality of electrodes. The stimulation current is provided such that a sum of respective time-varying moments at the plurality of motor units remains substantially constant and non-zero.

11 Claims, 21 Drawing Sheets

SYSTEM AND METHOD FOR STIMULATING MOTOR UNITS

RELATED APPLICATION

This application claims priority from U.S. Provisional Application No. 61/659,508, filed 14 Jun. 2012, the subject matter of which is incorporated herein by reference in its entirety.

TECHNICAL FIELD

The present invention relates to an apparatus and method for use of a system and method for stimulating motor units and, more particularly, to a system and method of stimulating a plurality of independent, mutually agonist motor units.

BACKGROUND OF THE INVENTION

Motor and sensory neuroprostheses using functional neuromuscular stimulation ("FNS") are important interventions in improving quality of life for individuals with spinal cord injury ("SCI") or other neuro-musculo-skeletal dysfunctions. For those with thoracic level injuries, FNS can restore standing and allow for significantly enhanced mobility. While these systems can facilitate short duration activities like transferring from one surface to another, their utility for longer duration activities such as prolonged standing has been inconsistent. Some neuroprosthesis users can stand for an hour or longer, while most are limited to five minutes or less, usually because of muscle fatigue and buckling at the knee joints. Multi-contact electrodes have the potential to increase muscle recruitment and improve the performance of FNS systems for standing after SCI and other applications (e.g., diaphragm pacing, grasp, seated trunk control, sensory assistance, or any other suitable applications). By selectively activating multiple populations of motor units within a muscle or synergistic group of muscles such as the quadriceps, these electrodes can more recruit the muscle, while also allowing for stimulation paradigms that delay the onset of fatigue.

For some individuals with low cervical or thoracic level SCI who maintain upper extremity function, FNS has been used to activate paralyzed muscles in the lower extremities to facilitate standing and transfers from one surface to another. These FNS standing systems have used surface, percutaneous, and implanted electrodes with varying degrees of success. One such system, known as Parastep (available from Sigmedics Inc. of Northfield, Ill.), uses surface stimulation to extend the knees and hips during standing, and has returned mobility to over 400 people with low thoracic level SCI. However, because the Parastep system relies on surface stimulation, its performance is hampered by a number of major limitations. First, surface electrodes must be placed on the skin before each use, leading to variability in the response to stimulation and the performance of the system from day to day. Further, surface stimulation cannot selectively activate muscles that are deep within the legs, such as the knee extensor vastus intermedius, without also activating more superficial muscles, such as the biarticular knee extensor and the hip flexor rectus femoris. This limitation reduces the choice of muscles for use in surface FNS systems, and constrains the types of movements that are possible with the Parastep.

Other FNS systems for standing that use intramuscular stimulating electrodes with percutaneous leads have been shown to repeatably provide sufficient knee and hip extension for standing, and can achieve significantly better selectivity than systems using surface electrodes. However, percutaneous electrodes have exit sites where leads pass through the skin, increasing infection risk and requiring significantly more daily care than surface electrodes. They are also prone to performance degradation over time as a result of migration of the electrode away from the desired motor point.

Fully implanted FNS systems offer advantages over both surface and percutaneous stimulation systems, in that electrodes can be placed to selectively stimulate virtually any muscle, and there are no exit sites or requirements for daily care of the system. Furthermore, there is a significant cosmetic advantage to a system that is entirely implanted under the skin, rather than on or through the skin surface. One such FNS system that has been developed uses an 8-channel implanted stimulator and muscle-based (intramuscular and epimysial) electrodes to restore standing and transfer function to individuals with low cervical and thoracic level SCI. The system, which has been implanted in 18 subjects as part of a Phase II clinical trial, stimulates bilateral knee extensors (vastus lateralis), hip extensors (gluteus maximus and semimembranosus), and trunk extensors (erector spinae) to extend the knees and hips and stabilize the trunk. With this system, some subjects have been able to stand with the aid of a walker for over 45 minutes at a time, and could release one hand from the walker to perform activities of daily living. System performance has been inconsistent across subjects, however, with most experiencing much shorter standing durations. In fact, for the 11 subjects who continued to participate in the research program for at least two years after implantation, more than half never achieved standing times greater than 5 minutes. Typically, standing times were limited by knee extensor fatigue and buckling of the knee joints, which are believed to be largely attributable to the use of muscle-based electrodes in stimulating only a portion of the available knee extensor musculature.

A major limiting factor in the maximum standing times observed with the first generation implanted standing neuroprosthesis is fatigue of the vastus lateralis muscle. In order to delay the onset of fatigue and improve the functionality of neuroprostheses for standing after SCI, it is important to understand the mechanisms of fatigue in electrically stimulated muscle, so that new techniques can be developed to maintain strong contractions for longer periods of time.

Muscle fatigue is the result of a combination of factors that can lead to a rapid decrease in the force generated in response to stimulation. These factors can affect transmission at the neuromuscular junction as well as excitation-contraction coupling within the muscle itself. At the neuromuscular junction, depletion of acetylcholine can reduce transmission of action potentials from motor neurons to the muscle fibers they innervate. Within the muscle, depletion of $Ca^{2+}$ stores, decreased pH as a result of lactic acid buildup, impaired impulse propagation through T tubules, and reduced availability of ATP as a result of oxygen and glycogen depletion can all cause impairment of excitation-contraction coupling. These factors can all occur simultaneously and can be highly dependent on the type of stimulation applied to the muscle. For example, constant high frequency stimulation has been demonstrated to cause impaired propagation of action potentials in the muscle, likely as a result of decreased blood flow and subsequent oxygen and ATP depletion, whereas intermittent low frequency tetanic stimulation can cause fatigue via depletion of and decreased sensitivity to $Ca^{2+}$. These mechanisms occur on a variety of time scales, with $Ca^{2+}$ depletion and restoration occurring on the order of seconds or faster, while oxygen and glycogen depletion can occur more slowly and have significantly longer lasting effects. In fact, constant low frequency stimulation has been demonstrated to induce significantly longer lasting fatigue, which can have effects on muscle strength 24 hours or more after it begins, with severe decreases in excitation-contraction coupling and damage to muscle sarcomeres suggested as potential mechanisms for this long-duration fatigue.

SUMMARY OF THE INVENTION

In an embodiment of the present invention, a system includes an electrode array. The electrode array includes a plurality of electrodes configured to provide stimulation to respective motor units of a plurality of independent, mutually agonist motor units. A stimulator assembly is configured to provide a stimulation current to each electrode of the plurality of electrodes. The stimulation current is provided such that a sum of respective time-varying moments at the plurality of motor units remains substantially constant and non-zero.

In an embodiment of the present invention, a system includes an electrode array, including N electrodes, where N is a positive integer greater than two. The electrode array is configured to provide stimulation to respective motor units of a plurality of independent, mutually agonist motor units. A stimulator assembly is configured to provide to each of the N electrodes an appropriate current to induce, at each of the N motor units, a sinusoidally-varying moment at a same frequency, with the sinusoidally-varying moment induced by an $i^{th}$ electrode of the plurality of electrodes having a phase shift of 2i*pi/N radians relative to the sinusoidally-varying moment induced by a first electrode of the plurality of electrodes.

In an embodiment of the present invention, a method for stimulating a plurality of independent, mutually agonist motor units comprises providing a first stimulation current to an electrode associated with a first motor unit of the plurality of motor units to induce a first sinusoidally-varying moment, having a first frequency, in the first motor unit. A second stimulation current is provided to an electrode associated with a second motor unit of the plurality of motor units to induce a second sinusoidally-varying moment, having the first frequency, in the second motor unit with a phase shift, relative to the first sinusoidally-varying moment, of 2*pi/3 radians. A third stimulation current is provided to an electrode associated with a third motor unit of the plurality of motor units to induce a third sinusoidally-varying moment, having the first frequency, in the third motor unit with a phase shift, relative to the first sinusoidally-varying moment, of 4*pi/3 radians.

BRIEF DESCRIPTION OF THE DRAWINGS

For a better understanding of the invention, reference may be made to the accompanying drawings, in which.

DESCRIPTION OF EMBODIMENTS

By altering the frequency or duty cycle of stimulation of muscles, it may be possible to differentially affect the causes of fatigue, such as by delaying the depletion of $Ca^{2+}$ stores or increasing oxygenation and ATP concentration in muscle tissue, to maintain strong muscle contractions and increase the time before fatigue.

Electrodes, such as nerve-cuff electrodes or any other desirable electrode currently known or later discovered, can be used and controlled under the present invention to achieve a stable, selective, chronic interface with the human peripheral nervous system, such as for control of a variety of muscles and functions. Examples of suitable applications of the present invention include, but are not limited to, controlling the ankle plantar- and dorsiflexors for walking and the muscles of the shoulder and arm for restoration of upper extremity function. Stimulation parameters for systems and methods like those of the present invention can be chosen to activate multiple agonist populations of motor units via one or more electrodes of any desired type (e.g., intramuscular, epimysial, or any other type of electrode), with each having one or more contacts.

Figure 1:
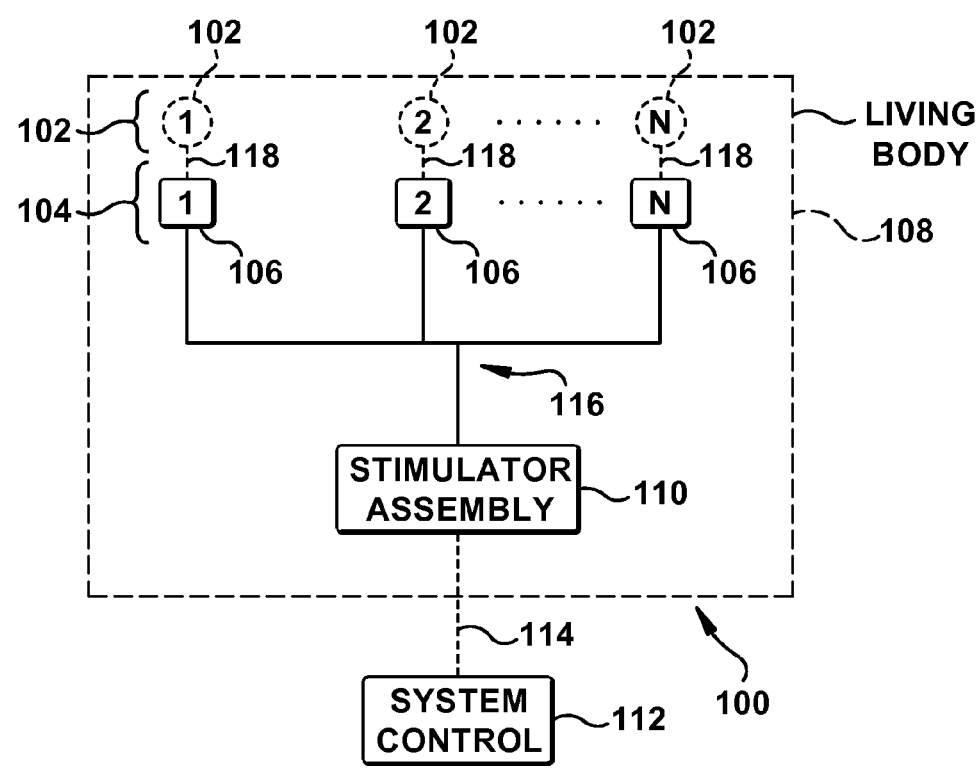
FIG. 1 is a schematic diagram of one embodiment of the present invention.

In accordance with the present invention, FIG. 1 depicts a system 100 for stimulating a plurality of independent, mutually agonist motor units 102. The system 100 includes an electrode array 104 comprising at least one, and preferably a plurality of, electrodes 106 of any suitable type. Only a few electrodes 106 of the electrode array 104 are shown in FIG. 1 as examples, but the electrode array may include N electrodes, with N being a positive integer greater than two. For example, N could be equal to three.

The electrodes 106 are each configured to provide stimulation to respective motor units 102 of at least one, and preferably a plurality of, mutually agonist motor units. For example, and as described herein, the motor units 102 are at least portions of muscles of a living body 108 (e.g., a single muscle or a group of muscles) and/or the nerves and fascicles associated therewith. A stimulator assembly 110 is configured to provide a time-varying current to each electrode 106 of the plurality of electrodes. Optionally, either or both of the electrode array 104 and the stimulator assembly 110 may be configured to be implantable within a living body 108.

Any desired control and power systems, located inside and/or outside the living body 108, may be provided to the system 100. For example, a system control 112, which can be external to the living body 108, may be configured to communicate with the stimulator assembly 110 to adjust at least a chosen one of a frequency, amplitude, and/or pulse duration associated with the time-varying current.

Connections between the various structures of the system can be made in any desired manner. For example, and as indicated by the dashed line 114 in FIG. 1, the system control 112 could wirelessly provide power and/or control signals from outside the living body 108 to the stimulator assembly 110 and/or the electrode array 104. The stimulator assembly 110 could be wired and/or wirelessly connected via linkage 116 to any or all of the electrodes 106. Likewise, the electrodes 106 could be wired and/or wirelessly connected (e.g., placed in direct contact and/or connected via intervening nerves) via linkages 118 to their respective motor units 102.

Figure 2A:
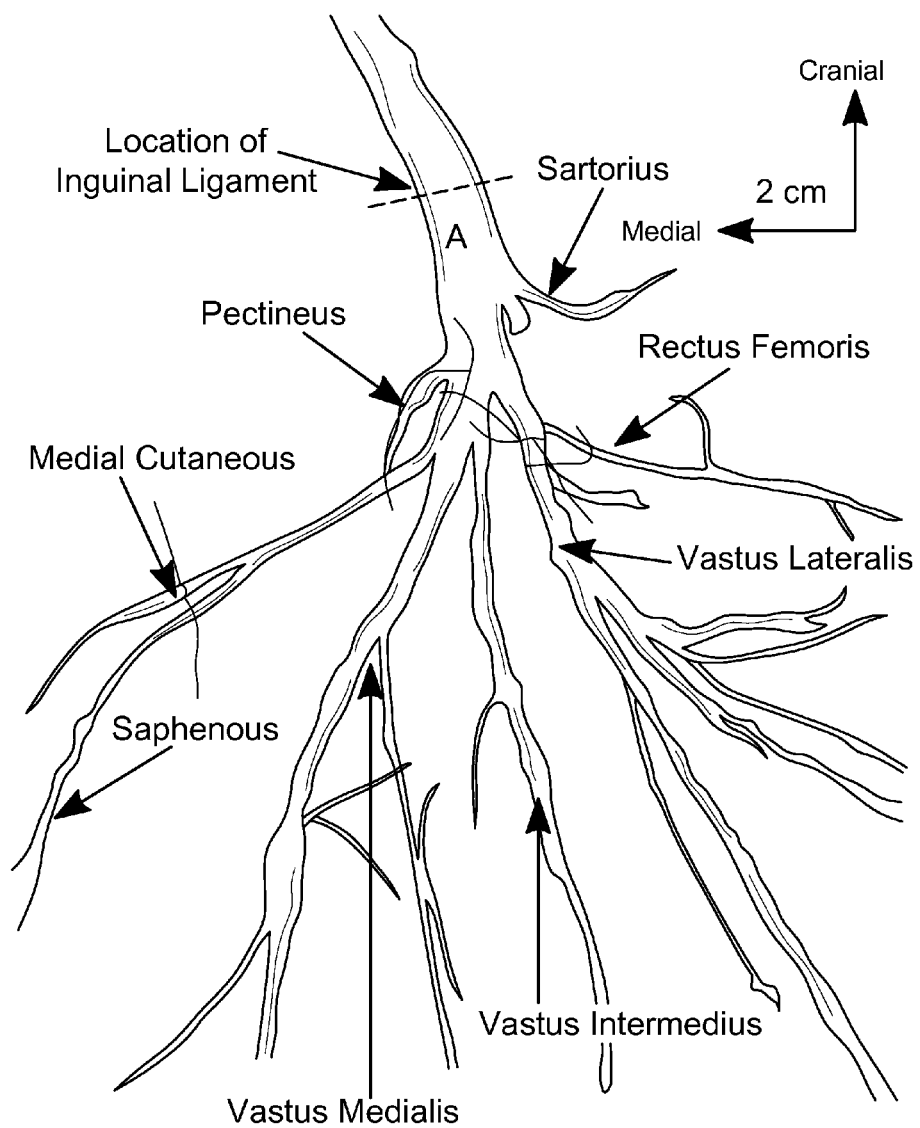
FIGS. 2A and 2B are labeled diagrams of a human femoral nerve which is an example use environment for the present invention.
Figure 2B:
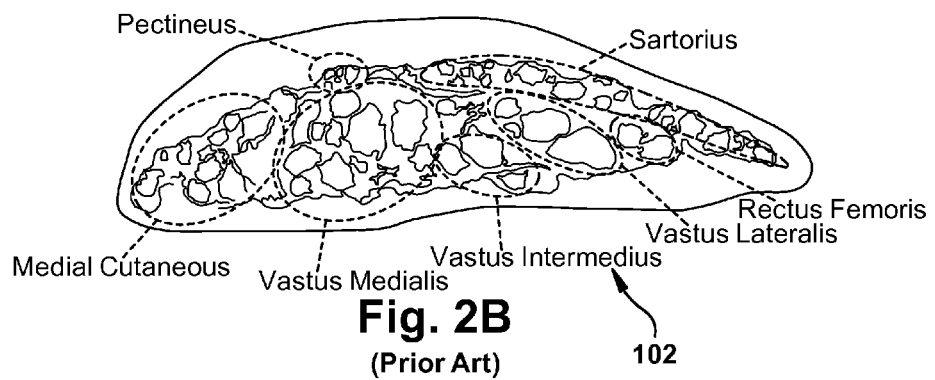

FIGS. 2A-2B are labeled depictions of the anatomy of the human femoral nerve, which will be used as an example of a motor unit 102 in the below description.

FIGS. 3A-4B depict suitable example electrodes 106 which can be used in conjunction with the present invention. In an attempt to increase standing time for users of the first generation implanted standing neuroprosthesis, the muscle-based electrodes 106 previously used to activate the knee extensor muscles (motor units 102) in previous work can be replaced with more proximally placed nerve-based electrodes 106 that include multiple contacts which can be controlled independently. It is believed that such nerve-cuff electrodes 106, when present, can more completely recruit the muscle tissue 102 of the quadriceps than a muscle-based electrode, and that the nerve-cuff electrodes can activate multiple independent muscle-fiber populations within the quadriceps which can be manipulated to produce longer maximum standing times.

Figure 3A:
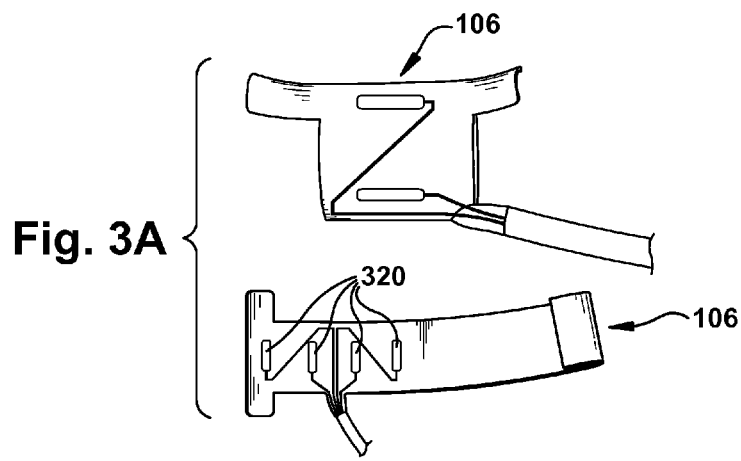
FIG. 3A depicts an example electrode in two configurations.
Figure 3B:
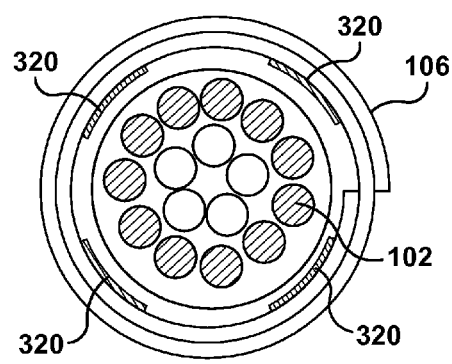
FIG. 3B schematically depicts the electrode of FIG. 3A in the use environment of FIGS. 2A and 2B.

One example type of cuff electrode 106 is shown in FIGS. 3A-3B. The four-contact self-sizing spiral nerve-cuff electrode 106 has a circular cross-section and four electrode contacts that are spaced equally around the circumference of the nerve. In other words, the electrode may be a spiral nerve cuff electrode configured to wrap around at least a portion of at least one nerve (which may be a femoral nerve) within the living body. The top electrode in FIG. 3A is shown in a compact, rolled-up configuration, and the bottom electrode in FIG. 3A is shown unrolled to reveal three of the individual contacts 320. The spiral nerve-cuff electrode 106 has been used both in animal experiments and in human subjects to selectively stimulate sensory nerves 102 as well as upper extremity motor nerves 102. In one study, the spiral nerve-cuff electrode 106 selectively activated individual fascicles 102 within a cat sciatic nerve to reproducibly achieve independent control of four separate fascicles innervating muscles in the hind limb.

To date, the spiral nerve-cuff electrode 106 has been implanted around the radial and musculocutaneous nerves 102 of three individuals with high cervical level SCI, to achieve the configuration shown schematically in FIG. 3B. Stimulation thresholds have been low and stable over at least three years after implantation, and each electrode 106 could selectively activate at least one muscle 102 to 28% of maximal activation without spillover to any other muscle. Further, this response was found to be highly stable, and the selectivity measured during intraoperative testing at the time of implantation was similar to that measured at three years after implantation.

Figure 4A:
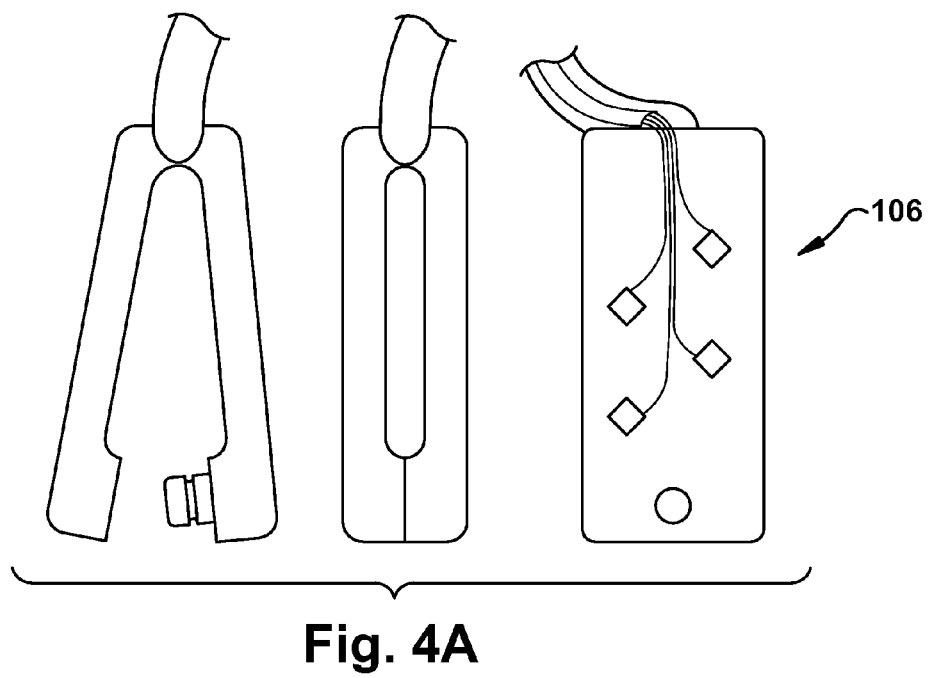
FIG. 4A depicts an example electrode.
Figure 4B:
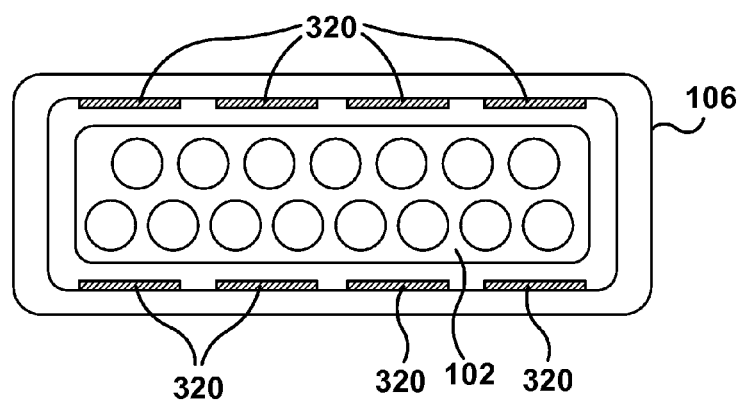
FIG. 4B schematically depicts the electrode of FIG. 4A in the use environment of FIGS. 2A and 2B.

Another example electrode 106 currently under development, the Flat Interface Nerve Electrode ("FINE") shown in FIGS. 4A-4B, is designed to further improve upon and address some limitations with the spiral nerve-cuff electrode 106. Specifically, because the cross-section of the spiral nerve-cuff electrode 106 is circular, as shown in FIG. 3B, it is well-suited for small circular nerves, but may not be as appropriate for larger and flatter nerves, such as the femoral nerve 102. This difference in geometry is especially important when the goal is to selectively activate individual fascicles 102 and their respective muscles with individual contacts within the nerve-cuff electrode 106. The round geometry of the spiral nerve-cuff electrode 106 means that some of the fascicles within the nerve will be near the center of the cross-section, as shown in FIG. 3B, and will be equally distant from all electrode contacts 320. With a biphasic square stimulation waveform, fascicles 102 closer to the perimeter of the nerve will be activated before those in the center. It might therefore be difficult to selectively activate the fascicles 102 located at the center of a nerve-cuff electrode 106 with a circular cross-section without first stimulating those closer to the electrode contacts 320. The FINE 106, shown in FIGS. 4A-4B, has a rectangular, rather than round, cross-section which aligns the fascicles 102 so that they are closer to the eight stimulating contacts 320.

In one study, when the FINE 106 was implanted around the sciatic nerves 102 of cats, the electrode 106 was able to selectively stimulate at least four separate muscles and could independently control the force output from each of those muscles. Realistic numerical simulations of a multi-contact FINE 106 on the human femoral nerve 102 demonstrated that an appropriately dimensioned FINE can selectively stimulate each of the six knee extensor and hip flexor muscles innervated by that nerve. Also, in acute intraoperative testing where the FINE 106 was placed on the femoral nerves 102 of able-bodied human subjects, at least four of the six knee extensor and hip flexor muscles were activated independently in all subjects.

Another example of a suitable electrode is a 100-contact slant electrode array 104 (not shown) available from the University of Utah in Salt Lake City, Utah.

Regardless of the specific type of electrodes 106 used (whether those listed herein or those known to one of ordinary skill in the art), one example FES system uses a suitable type of electrode 106 to provide electrical signals to the erector spinae 102 for trunk stabilization, the gluteus maximum 102 and posterior portion of the adductor magnus 102 for hip extension, and the vasti 102 (e.g., via a femoral nerve-cuff) for knee extension.

It has also been found that simultaneous stimulation, using, for example, nerve-cuff electrodes 106, produces significantly stronger muscle 102 contractions and higher joint moments than stimulation through a muscle-based electrode. In addition, in some cases, it is possible to selectively recruit at least three populations of motor units 102 associated with a certain muscle, such as within the uniarticular heads of the quadriceps. The ability to selectively activate independent populations of motor units 102 is highly dependent on both the anatomy of the nerves and the orientation of the electrode (e.g., the cuff) 106 with respect to the nerve, so results may be variable from individual to individual and even within a single individual.

In addition, it has been found that the amount of overlap between pairs of contacts 320 within multiple electrodes (e.g., nerve-cuff electrodes) 106 can vary over time. These variations can occur as a result of changes in the electrode-nerve interface, but also or instead can occur because the relative strength of the response through individual contacts is used in the calculation of overlap. This latter factor means that variations in strength of the stimulated response over time may affect the amount of overlap between contacts 320. Accordingly, retuning of desired stimulation parameters may be periodically desirable, but even over an extended period of time, overlap should still remain low between pairs of contacts 320.

The selection, configuration, and control of the time-varying current provided to the motor units 102, particularly the induction of time-varying moments in the agonist motor units in response to this current, is of interest to the present invention and will now be discussed in detail with reference to FIGS. 5-19.

I. Selection of Selective Stimulation Parameters for Multi-Contact Electrodes

In Section I of this Description of Embodiments, overlap between pairs of contacts is quantified by the deviation in their combined response from linear addition of individual responses. Simple mathematical models are fit to recruitment and overlap data, and a cost function is defined to maximize recruitment and minimize overlap between all contacts. Results are presented for 4 four-contact nerve-cuff electrodes stimulating bilateral femoral nerves of two human subjects with spinal cord injury. Knee extension moments between 11.6 and 43.2 Nm were achieved with selective stimulation through multiple contacts of each nerve-cuff with less than 10% overlap between pairs of contacts. The overlap in stimulation measured in response to selective stimulation parameters was stable at multiple repeated time points after implantation. These results suggest that the method described here can provide an automated means of determining stimulus parameters to achieve strong muscle contractions via selective stimulation through multi-contact peripheral nerve electrodes.

I.1 Introduction

Multi-contact stimulating electrodes have been gaining popularity as a means for interfacing with peripheral nerves in functional neuromuscular stimulation (FNS) systems. These electrodes allow for a high density of contacts to be placed around or in peripheral nerves to independently activate multiple fascicles and motor units. Independent activation can allow for the control of multiple functions with a single electrode and for recruitment of multiple populations of agonist motor units within a single muscle. Control of multiple functions with a single electrode could reduce the number of implantation sites required to produce a variety of functional joint moments for FNS systems. Control of multiple agonist motor unit populations with a single electrode could allow for better control of joint moment by varying the number of motor units recruited by the electrode. Further, by alternating stimulation of multiple agonist motor unit populations, it may be possible to reduce stimulation duty cycle and prolong the time of muscle contractions before the onset of fatigue. To accomplish these benefits of multi-contact electrodes, it is helpful to be able to measure and minimize overlap in stimulation between the contacts within these electrodes. Overlap in stimulation can degrade the ability to control the response to stimulation and can lead to overly rapid fatigue if motor units are stimulated repeatedly by multiple contacts.

I.i.1 Quantifying Selectivity of Stimulation

Determining selective stimulation parameters when multiple contacts stimulate agonist populations of motor units is a complex problem. Populations of agonist motor units cannot be separated based on their lines of action or resultant joint moments. If the spatial relationship between the electrode and the fascicles within the nerve was known a priori, it would be possible to select stimulation parameters based on estimates of activation of the neural tissue. The femoral nerve, however, has a highly branched structure (FIG. 2A), and there is a high degree of person-to-person variability in the anatomy of the nerve, both in branching structure and in the location of fascicles within the nerve that innervate specific muscles. Because current state-of-the-art imaging technology is insufficient to accurately visualize the structure of the nerve in vivo, it is not possible to know what the spatial relationship is between the contacts within a nerve-cuff electrode and the fascicles and respective muscles the electrode will activate. Stimulation overlap must, therefore, be inferred from indirect measurements. One commonly used indirect method of determining selective stimulation parameters is to record the electromyogram ("EMG") response to stimulation via intramuscular recording electrodes. This technique provides information on which muscles are responding to stimulation through each contact of an electrode, but has significant limitations. The amplitude of the EMG signal is dependent not only on the activation level of the target muscle, but also the specific placement of the EMG electrode relative to the activated fibers. As a result of this dependence, the EMG signal is usually normalized, which means that it is not possible to determine the relative activation and resultant force production of one muscle with respect to another muscle. Therefore, while it is possible to gain general information about which muscles are activated by an electrode, the method provides little functionally relevant information concerning the force production of target muscles. Further, because of limits in spatial resolution of the EMG electrodes, it is possible that two non-overlapping populations of motor units may appear to overlap because they are both close to the recording electrode.

Another method for quantifying selectivity takes advantage of the concept that motor units in their absolute refractory period, which lasts between 1.5 and 2.1 ms, will not respond to stimulation. Therefore, if a stimulus pulse is applied through one electrode contact within 2.1 ms after a pulse is applied through another electrode contact, motor units activated by the first stimulus will not respond to the second stimulus. This means that, if there is overlap in the stimulation fields of two contacts, the resultant force generated when one contact is fired within 2.1 ms after the other will be less than the linear sum of the individual forces when each contact is fired separately.

Conversely, the forces generated by stimulating two completely independent populations of motor units will add linearly, even if one population is stimulated while neurons from the other population are in their absolute refractory period. By varying stimulation parameters including pulse amplitude and pulse width, it may be possible to minimize the deviation from linear addition, and thereby minimize stimulation overlap, while maximizing the magnitude of the force generated by each independent motor unit population to selectively produce strong muscle contractions to lock the knees and improve FNS-assisted standing.

While this method provides a useful way to quantify overlap between two contacts, it does not easily scale to larger numbers of contacts. To create a metric of overall overlap for an entire multi-contact electrode, others have used this method to quantify overlap between pairs of contacts within the electrode, and then averaged all of those overlaps. While this method provides some insight into the general amount of overlap for a multicontact electrode, it does not provide a clear means of tuning stimulation parameters for each individual contact to reduce overlap while generating functionally useful stimulated joint moments. Furthermore, as the number of contacts within the electrode increases, the number of pairwise combinations of contacts that must be considered for this method increases exponentially. This can quickly lead to impossibly large data sets as the number of contacts increases.

In Section I, a method for choosing optimal selective stimulation parameters for multi-contact electrodes that minimizes overlap between adjacent contacts while maximizing the joint moment produced by stimulating through each contact is described. The method described above can be used to quantify overlap between pairs of contacts, with the addition of a set of mathematical models to reduce the data requirements for characterizing the electrodes, and a cost function that acts to minimize all pairwise overlaps while simultaneously maximizing all joint moments. This method can efficiently characterize overlap and selectivity for multi-contact electrodes to produce strong muscle contractions with little or no overlap between stimulated motor unit populations. While the method is designed to accommodate electrodes with high densities of contacts, it can be tested clinically with the four contact spiral nerve-cuff electrode mentioned above. The method can select stimulation parameters that generate strong contractions with low overlap for this electrode, and that the selective responses are stable over months after implantation of the electrodes.

I.ii Methods

The process for quantifying and optimizing selective stimulation for multi-contact electrodes includes four fundamental steps. First, the response to stimulation through the multi-contact electrode and the overlap between pairs of contacts are quantified. These responses are twitches, elicited by single stimulus pulses, which are less likely to cause fatigue and can be collected more quickly than tetanic responses. Next, the relationship between responses to twitch and tetanic stimulation is quantified. This relationship provides a scaling factor so that the twitch responses, which are more easily collected, can be converted to more functionally relevant tetanic responses. Third, mathematical models are fit to the scaled recruitment and overlap data. These models serve the dual purposes of reducing the size of the data set required for optimization and providing a mathematical framework over which optimization can be performed. Finally, the scaled recruitment and overlap models are used as inputs to a cost function that can be minimized to provide optimal selective stimulation parameters.

I.ii.1 Subject Selection and Multi-Contact Electrodes

The self-sizing four contact spiral nerve-cuff electrode shown in FIGS. 3A-3B was used to develop and test this method for optimizing selective stimulation parameters. A total of four nerve-cuffs were implanted chronically around bilateral femoral nerves to stimulate the knee extensors of two volunteers with motor-complete spinal cord injury (Subject I: level C7, ASIA B and Subject 2: level TI1, ASIA B). The nerve-cuffs, which have four contacts that can be controlled independently, were sized so that any two adjacent contacts were separated by 90° around the circumference of the nerve. All contacts were connected to an implanted stimulator capable of generating monopolar, charge-balanced biphasic stimulus pulses. All stimuli had current amplitudes of 1.4 mA for Subject I and 0.8 mA for Subject 2, because, of the available stimulation amplitudes from the implanted stimulator, these provided the largest range between the threshold and saturation responses to stimulation.

I.ii.2 Recruitment and Overlap Characterization

For the first step in optimizing selective stimulation parameters, the response to stimulation and the overlap between pairs of contacts were characterized. With the knee fixed at 20° of flexion and one axis of a 6 degree-of-freedom load cell aligned with the knee joint center, isometric knee extension moment was recorded in response to stimulus pulses applied to the femoral nerve through each contact of the cuff electrodes.

Data were low-pass filtered at 31.25 Hz and sampled at 150 Hz.

Figure 5:
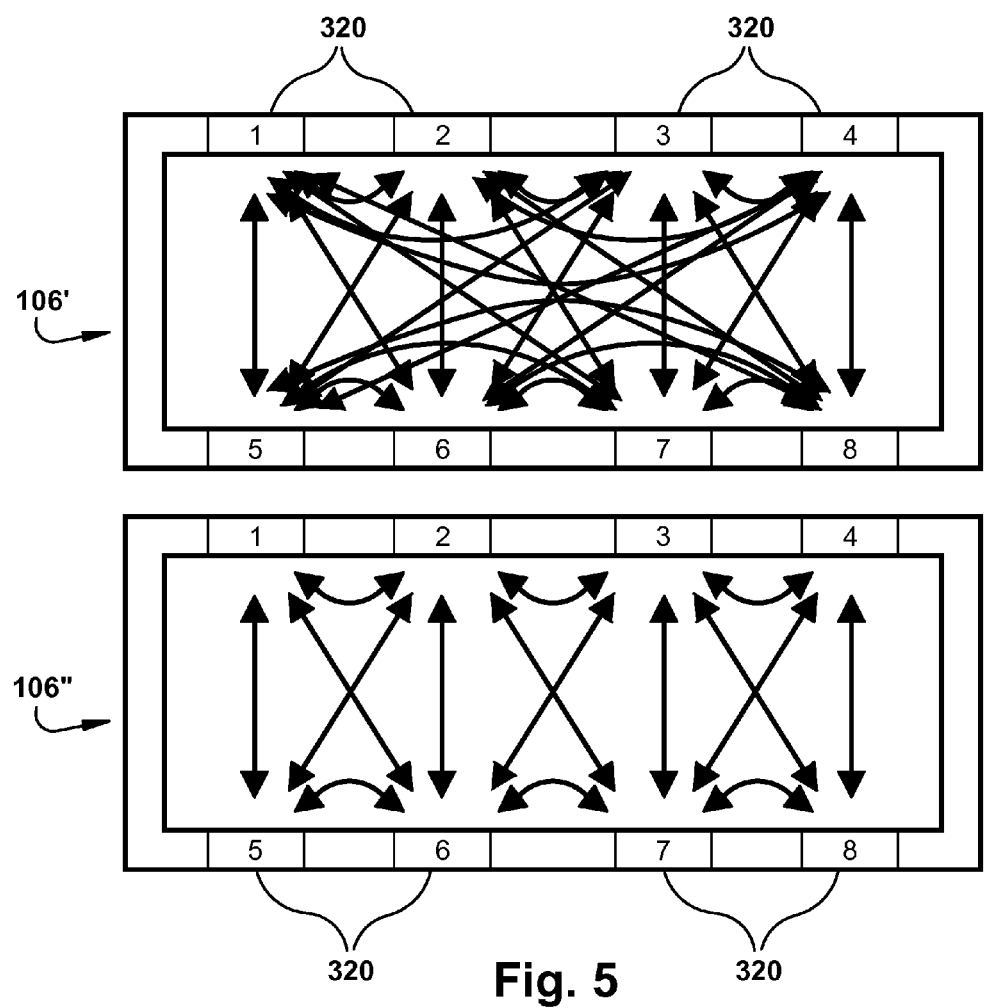
FIG. 5 is a schematic diagram of two electrodes and their corresponding pair combinations.

To characterize the response to stimulation, pulse width modulated recruitment curves were collected. To characterize overlap between pairs of contacts, a stimulus pulse was applied through one contact, followed by a 2 ms time delay, and then a pulse through a second contact. The pulse widths of all stimuli were varied between 1 and 255 us. For some multi-contact electrodes, it is possible to reduce the size of the data set by eliminating pairwise combinations of contacts that are not adjacent to each other, since elimination of overlap between adjacent contacts will also eliminate overlap between nonadjacent contacts. For example, in the case of an eight contact FINE, this would reduce the number of possible pairwise combinations from 28 to 16, as shown in FIG. 5. (Note that for a pair of contacts, there are two possible pairwise combinations of contacts if the order of stimulation is taken into account. For example, for contacts A and B, either A or B could be stimulated first. In these experiments only one of the possible pairwise combinations was considered.) In the case of the four-contact nerve-cuff, all contacts are adjacent to each other, so all six pairwise combinations can be considered.

I.ii.3 Twitch/Tetanic Relationship

While the twitch response to stimulation can be collected far more quickly and with less likelihood of causing fatigue, the tetanic response to stimulation is more functionally relevant. Studies in both animals and humans have demonstrated that there is a linear relationship between the shape of isometric twitch and tetanic recruitment curves, and that a simple linear scaling factor can describe the difference between these. To quantify this scaling factor, twitch and tetanic responses to stimulation were recorded with the knee held in 20° of flexion. The ratio of the maximum twitch and tetanic responses was used as a scaling factor. Further details of this method are described elsewhere.

I.ii.4 Mathematical Models of Recruitment and Overlap

Fitting mathematical models to recruitment and overlap data reduces the size of the data set required for characterizing the electrodes while also providing a framework for optimization of stimulation parameters. To determine the best form of functions for recruitment and overlap, subsets of 32 recruitment or overlap data points were fitted to a variety of models and separate subsets of 16 data points were used to test for goodness-of-fit ("GOF"). For recruitment data, 1st through 5th order polynomial, sigmoid, Gaussian, and Gompertz functions were tested. For overlap data, which are two-dimensional since pulse width can be controlled for both contacts in a pairwise combination, 1st through 5th order two-dimensional polynomials were tested. To determine GOF, coefficients of determination ($R^2$), and the corrected Akaike Information Criterion (AICc) were calculated for each model. AICc is a measure of how well a model fits a set of data relative to the number of parameters in that model. It compares all models for a given set of data, and ranks them based on GOF and number of parameters. Models that achieved the best fits were selected for implementation in the optimization described below.

I.ii.5 Optimization of Selective Stimulation Parameters

Achieving selectivity of stimulation necessarily creates a trade-off between large stimulus levels with large joint moments and small stimulus levels with low overlap. It is, therefore, useful to treat selectivity as an optimization problem, where the goal is to choose the best stimulation parameters to maximize joint moment while minimizing overlap, using a cost function of the form $$C(\overline{PW}) = -\omega_0 M_T(\overline{PW}) + \omega_1 O_T(\overline{PW}) \quad \text{(Eq. 1)}$$

where PW is an N-dimensional vector of pulse widths of stimulus pulses for an N-contact electrode, $O_T$ quantifies the overlap of all contacts within the electrode, $M_T$ quantifies the joint moment generated by all contacts within the electrode, and $\omega_0$ and $\omega_1$ are weighting factors. The joint moment term, MT, is defined here as $$M_T(\overline{PW}) = \frac{\Sigma i = 1:N \; M_i(PW_i)}{\Sigma i = 1:N \; \max(M_i)} \quad \text{(Eq. 2)}$$

where Mi is the moment generated when stimulating through contact i, which is described mathematically by the model function previously fit to recruitment data. The sum of these functions is divided by the sum of the maxima of the functions to normalize the joint moment term. In this way, overall joint moment is normalized with respect to the overlap term, but joint moments from each of the contacts are treated equally with respect to each other.

Overlap for a pair of contacts is quantified by the deviation from linear addition when stimulation is applied through one contact shortly after stimulation through another contact. This can be expressed as $$M_{i \cap j}(PW_i, PW_j) = M_i(PW_i) + M_j(PW_j) - M_{i \cup j}(PW_i, PW_j) \quad \text{(Eq. 3)}$$

where $M_{i \cap j}$ is the overlap between contacts i and j, $M_i$ and $M_j$ are the moments generated when stimulating through contacts i and j, respectively, and $M_{i \cup j}$ is a mathematical function fit to the moment generated when stimulating through two contacts with a short time delay. To take all of these pairwise overlaps into account, while normalizing the overlap so that its weighting is controlled relative to $M_T$, $O_T$ is defined as $$O_T(\overline{PW}) = \frac{2}{N^2 - N} \sum_{i=1:N-1} \sum_{j=2:N} \frac{M_{i \cap j}(PW_i, PW_j)}{M_{i \cup j}(PW_i, PW_j)} \quad \text{(Eq. 4)}$$

which ranges between 0 and 1.

Since both OT and MT are normalized, the weighting factors, $\omega$, can be used to emphasize larger joint moments or lower overlap, depending on the particular application. In an example of the present invention, the terms were weighted equally.

To ensure that either sufficiently large joint moments or sufficiently small overlaps are achieved, a linearly increasing penalty was added to the function if joint moment for any contact was less than 5 Nm or overlap was greater than 10% between any two contacts.

A direct search optimization algorithm was used to find the minimum of the cost function, and the optimal set of pulse widths for selective stimulation.

I.ii.6 Stability of Overlap

To achieve reliable control in an FNS system, it is important that the response to stimulation is stable over time. Selectivity is a function of both muscle strength and stimulation overlap. While it is expected that muscle strength will change over time as the user exercises and builds muscle mass, if the interface between the electrode and nerve is stable, overlap is less likely to change over time. To test the stability of stimulation, the amount of overlap between pairs of contacts was quantified at multiple time points after implantation.

At the first time point, optimal stimulation parameters were chosen by the algorithm described above, and at each subsequent time point, overlap in stimulation between all pairs of contacts was measured using those same stimulation parameters. A one-tailed Student's t-test was used to determine if the mean overlap for any pair of contacts was greater than 10%.

I.iii Results

I.iii.1 Electrode Characterization and Mathematical Models

Figure 6A:
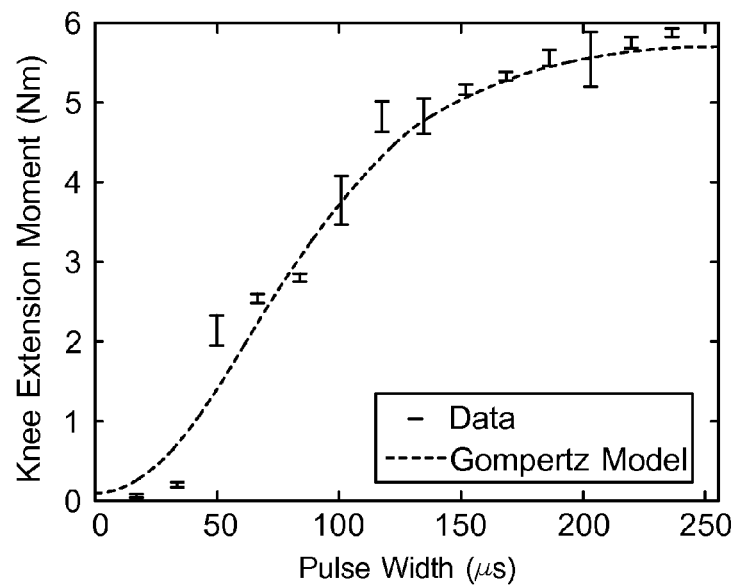
FIGS. 6(a)-9 and 12-19 graphically depict various test results of muscle stimulation.

Shown in FIG. 6(a) are the responses to stimulation through one contact of a nerve-cuff electrode (dots) and a Gompertz model fit to those data (line). FIG. 6(c) shows the average $R^2$ and AICc calculated for all eight contacts within the four nerve-cuff electrodes. Since AICc is a ranking of the appropriateness of each of the models, it ranges from 1 to 8, with 1 being the worst model and 8 being the best. From these results, the Gompertz function achieves the best GOF ($R^2=0.98\pm0.01$) and is the most appropriate model of the response to stimulation.

Figure 6B:
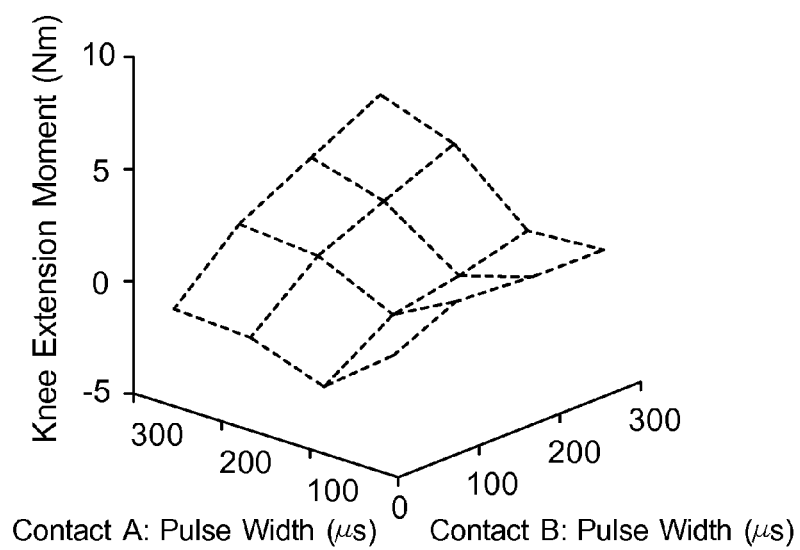
Figure 6C:
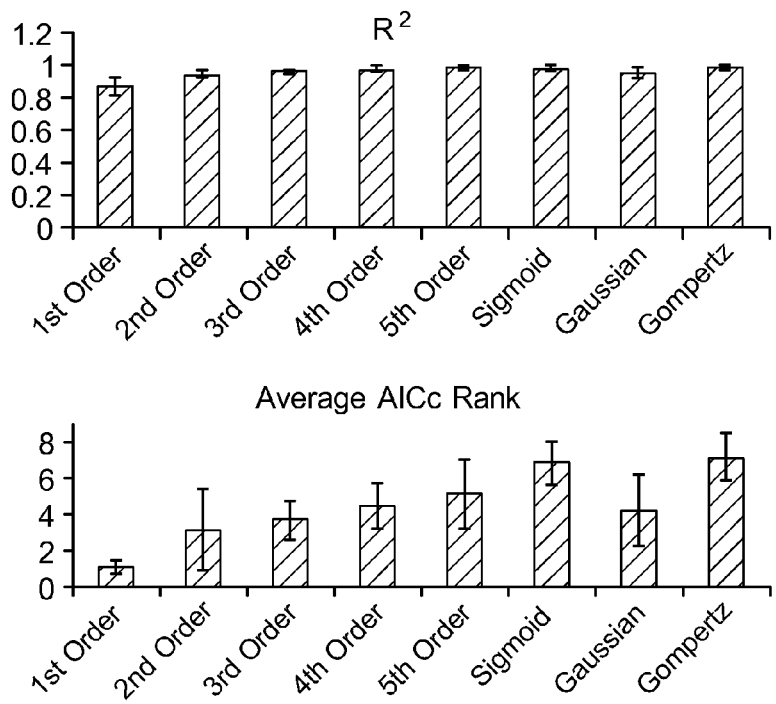
Figure 6D:
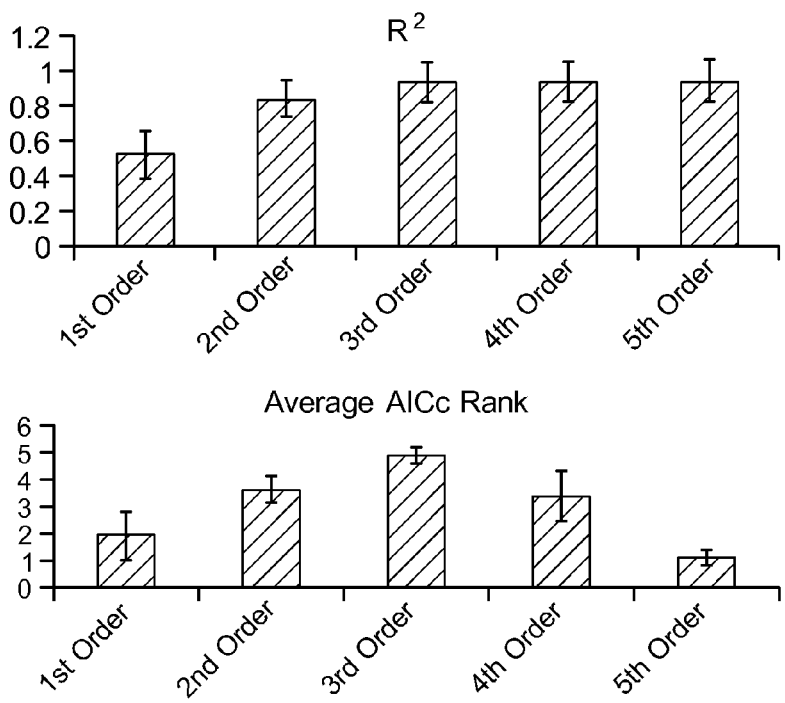

Shown in FIG. 6(b) is an example of overlap data between two contacts within one of the nerve-cuff electrodes (dots) as well as an example of a third-order polynomial model fit to those data (dashed lines). FIG. 6(d) shows the average $R^2$ and AICc calculated for all pairwise combinations of contacts for all four nerve-cuff electrodes. From these results, the third-order polynomial is the most appropriate model of the overlap in stimulation between two contacts ($R^2=0.92\pm0.11$) with the highest average AICc ranking.

I.iii.2 Twitch/Tetanic Relationship

Figure 7:
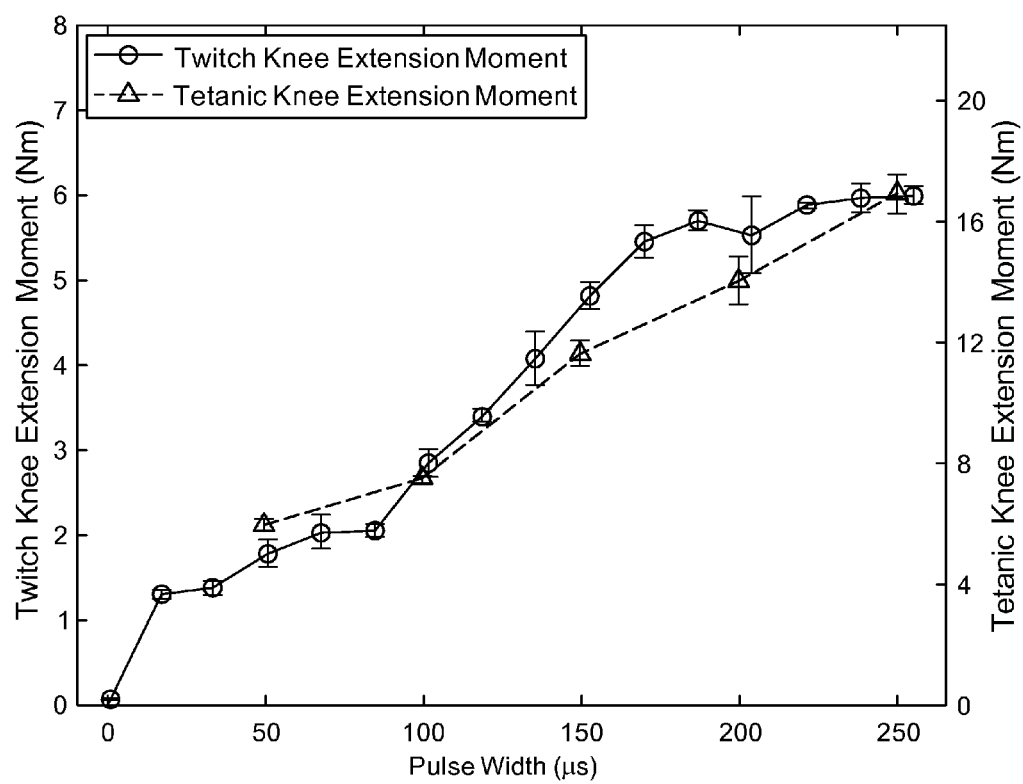

Examples of typical twitch and tetanic recruitment curves are shown in FIG. 7. For all sixteen contacts within the four nerve-cuff electrodes, the shape of the twitch recruitment curve was similar to the tetanic curve, and a linear scaling factor was calculated as the ratio of the maxima of the two curves (mean±standard deviation=2.56±0.55).

I.iii.3 Optimization of Selective Stimulation Parameters

Figure 8:
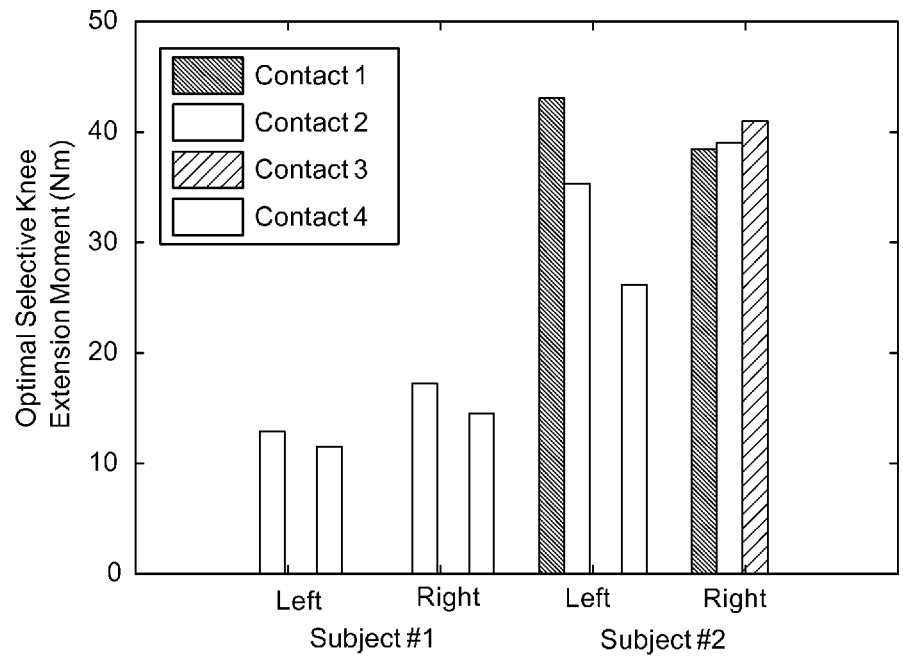

Shown in FIG. 8 are the joint moments produced by stimulating through each nervecuff contact using the optimal stimulation parameters for all nerve-cuff electrodes. As determined by a direct search of the previously defined cost function. Every pairwise combination of contacts within each electrode had less than 10% overlap.

Note that, in Subject 1, only two of four contacts, and in Subject 2, only three of four contacts for either electrode have non-zero stimulus parameters. The results of the optimization consistently demonstrated that removing these one or two contacts from the cost function produced significantly higher joint moments with less overlap than if all contacts were included or other contacts were removed. For contact 3 of the left nerve-cuff electrode in Subject 2, there was never any measurable motor response to stimulation.

I.iii.4 Stability of Overlap

Figure 9:
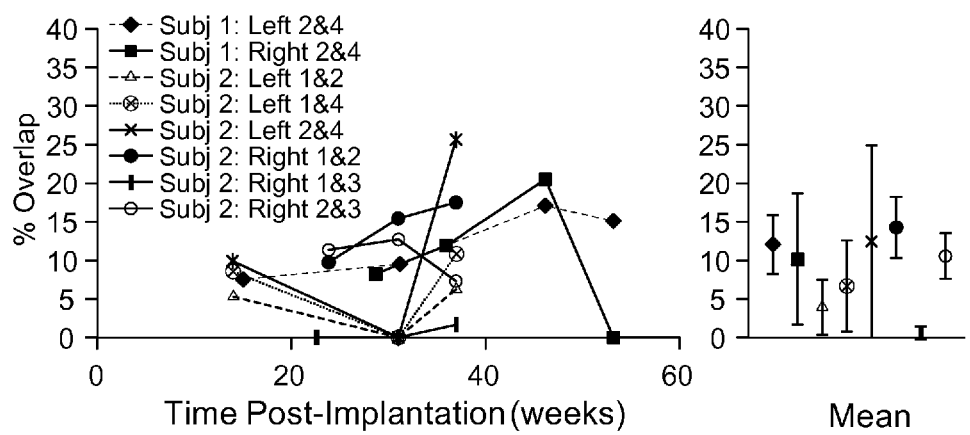

Shown in FIG. 9 are measurements of overlap in stimulation for contacts within the four nerve-cuff electrodes at multiple time points after implantation along with the mean±standard deviation for those measurements. Overlap was measured using the optimal selective stimulus parameters quantified at the first time point, so only contacts that produced optimal selectivity at that time were included in subsequent measurements. Therefore, only overlaps for two and three contacts for subjects 1 and 2 respectively are shown. Overlap between most pairs of contacts remained low and constant over time, with only three pairs demonstrating standard deviations greater than 5%. A Student's t-test did not demonstrate that mean overlap was statistically greater than 10% for any contact.

I.iv Discussion

The methods presented herein are designed to optimize stimulation parameters for multi-contact peripheral stimulating electrodes. Results presented here demonstrate that this method can select a set of stimulation parameters that provide strong muscle contractions with low overlap. In the case of these four nerve-cuff electrodes, the optimization determined that it is possible for two or three contacts to produce at least 11.6 Nm, but possibly as much as 43.2 Nm of knee extension moment with less than 10% overlap between pairs of contacts. Biomechanical models of standing with FNS estimate that as much as 27% body weight (BW) of knee extension moment is required to keep the knees locked during standing. For Subjects 1 (BW=57.2 kg) and 2 (BW=93.8 kg), this means 15.4 and 25.3 Nm, respectively, would be needed to maintain standing with FNS. Given that this moment is divided across two legs, and that the sum of selective moments for anyone of the nerve-cuff electrodes in this study is greater than these requirements, these results suggest that each subject should be able to stand with these selective joint moments with a significant excess maintained in reserve. Further, these joint moments should be large enough to allow for the implementation of stimulation paradigms such as carousel or interleaved stimulation that delay the onset of fatigue by reducing duty cycle or frequency of stimulation. If the joint moments were not sufficient to maintain standing or allow for the implementation of fatigue-delaying stimulation paradigms, it is possible to tailor the results of the optimization by adjusting weighting factors in the cost function to favor larger joint moments at the cost of tolerating more overlap.

While the optimization method described here was applied to an electrode with only four contacts, it was designed to be scalable to much higher density electrodes. By focusing only on overlap between adjacent pairs of electrodes, and by fitting mathematical models to both overlap and recruitment, it should be possible to select optimal stimulation parameters for electrodes with many more contacts without becoming prohibitively data intensive. If nonadjacent pairwise combinations of contacts were ignored and a limited data set was used to fit the Gompertz and third-order polynomial models, which have three and ten parameters, respectively, the method described above would require approximately 13 hours to completely optimize selective stimulation for a 100 contact Utah array, as compared to 11.6 days otherwise. This time requirement is a worst case scenario that only applies if every contact within the electrode activates an agonist population of motor units. In reality, it is likely that many contacts could be removed from the optimization because they activate either sensory neurons or non-agonist populations of motor units. Furthermore, the method used here to identify the relationship between twitch and tetanic recruitment was chosen because of its simplicity, but not its efficiency. In fact, of the 13 hours required to optimize a 100 contact Utah array, nearly 70% of that time would be devoted to characterizing the relationship between twitch and tetanic responses. Other methods known to one of ordinary skill in the art require significantly less time to characterize the relationship between twitch and tetanic responses, and could reduce the worst-case scenario time to completely optimize a 100 contact electrode to approximately six hours.

It should be noted that in the case of all four nerve-cuff electrodes, the optimization produced better results if either one or two contacts were eliminated from the optimization. In the case of Subject 1, the two contacts used in the optimization sit opposite one another around the circumference of the nerve, so it is reasonable to expect that they would have less overlap with one another than contacts that are directly adjacent. In the case of Subject 2, one of the contacts that was excluded never demonstrated any motor response to stimulation, which suggests the contact may have been located near sensory neurons or connective tissue. The results of the optimization were stable over time, with the amount of overlap between the included pairs of contacts remaining largely constant. This suggests that the nerve-cuff electrode provides a stable interface with the nerve.

I.v Conclusions

A method is presented in Section I for optimizing stimulation parameters for multi-contact peripheral stimulating electrodes. By collecting twitch responses to stimulation and fitting mathematical models to recruitment and overlap data, the method reduces the data requirements for characterizing and optimizing selective stimulation. The use of a cost function that includes terms representing both recruitment and pairwise overlap for all contacts within the electrode allows for maximization of the moments generated by all contacts while simultaneously minimizing the overlaps between all pairs of contacts. This method allows for an objective and automated means of selecting stimulation parameters for electrodes with high-densities of contacts, where manual selection of stimulation parameters would be prohibitively time intensive.

The results discussed in Section I also suggest that it is possible to generate strong contractions with little or no overlap between contacts within a four contact spiral nerve-cuff electrode. For the electrodes discussed herein, it was possible to produce between 11.6 and 43.2 Nm of selective knee extension moment with less than 10% overlap between contacts. These joint moments would likely be sufficient to keep the knees locked during standing, with significant reserves to allow for the implementation of fatigue-delaying stimulation paradigms.

Overlap in stimulation was also found to be stable over months after implantation, with little variation in overlap in response to the same stimulus parameters applied at multiple time points after implantation. This suggests that the spiral nerve-cuff electrode provides a stable interface with the nerve with little change in the stimulated response over time.

[end of Section I]

II. Advanced Stimulation Paradigms for Delaying the Onset of Fatigue

Section II of this Description of Embodiments describes the implementation and testing of advanced stimulation paradigms designed to delay the onset of fatigue and increase maximum standing time in users of FNS systems for standing after SCI. Advanced stimulation paradigms including carousel and interleaved stimulation, as well as a paradigm referred to here as the sum of phase-shifted sinusoids ("SOPS"), were implemented using multi-contact nerve-cuff electrodes wrapped around the femoral nerves of two individuals with motor-complete spinal cord injury. Fatigue tests were performed to determine the ability of each paradigm to prolong the duration of muscle contraction before fatigue.

While there appears to be a trend in the FNS art towards longer contractions with advanced stimulation paradigms as compared to constant stimulation, there were no statistically significant differences in any fatigue metrics calculated here.

In both subjects, it was possible to produce joint moments that were large enough for short duration (<1 min) standing, and one subject could stand for at least 10 minutes with each paradigm, though it is unclear if any paradigm had the ability to prolong standing time before fatigue as compared to constant stimulation.

The results discussed herein confirm that it is possible to implement advanced stimulation paradigms with selective multi-contact nerve-cuff electrodes, and suggest that these stimulation strategies may be able to delay the onset of fatigue in human users of FNS systems.

II.1 Introduction

FNS is an intervention that has been shown to have an important impact on the lives of individuals with SCI. By electrically activating paralyzed muscle, FNS can restore function and facilitate participation in a variety of activities of daily living ("ADLs") that would not otherwise be possible. For individuals with low cervical or thoracic level SCI who maintain good upper extremity function, FNS of the trunk and lower extremities can be used to restore standing, which allows for increased mobility and a reduction in the secondary health complications commonly associated with SCI.

Currently available FNS systems for standing utilize maximal levels of constant stimulation at the hips and knees. These high and unchanging stimulus levels provide a safety factor to ensure the knees remain locked during standing, but often at the cost of overly rapid fatigue and reduced standing times. One such system has been implanted in 18 individuals with SCI. While some users of this standing system have been able to stand for 30 minutes or longer, most have experienced standing times of five minutes or less, with a median standing time across all users of approximately three minutes.

While the relatively short standing times achievable with continuous stimulation are sufficient for facilitating transfers from one surface to another and accomplishing some ADLs, many positive outcomes, including the health benefits of weight bearing, the mobility in wheelchair inaccessible environments with a swing-to gait, and the ability to participate in other important social, work, and personal activities necessary to resume an active and independent lifestyle require durations longer than 10 minutes.

There is a growing body of evidence that advanced stimulation paradigms, which reduce the duty cycle or frequency of stimulation, can delay the onset of fatigue and prolong the duration of muscle contractions in a variety of applications including standing. One such paradigm (shown in FIG. 10(a)) is carousel stimulation, first proposed in 1974, in which stimulation is alternated between multiple populations of motor units to maintain a constant submaximal contraction at a reduced duty cycle.

This paradigm was originally developed for phrenic nerve pacing as part of a diaphragm stimulation system, and has been used to condition the latissimus dorsi to be more fatigue resistant as part of a "circulatory assist" stimulation system. The paradigm has not to date been used as part of a motor systems neuroprosthesis to delay the onset of fatigue in humans.

Figure 10A:
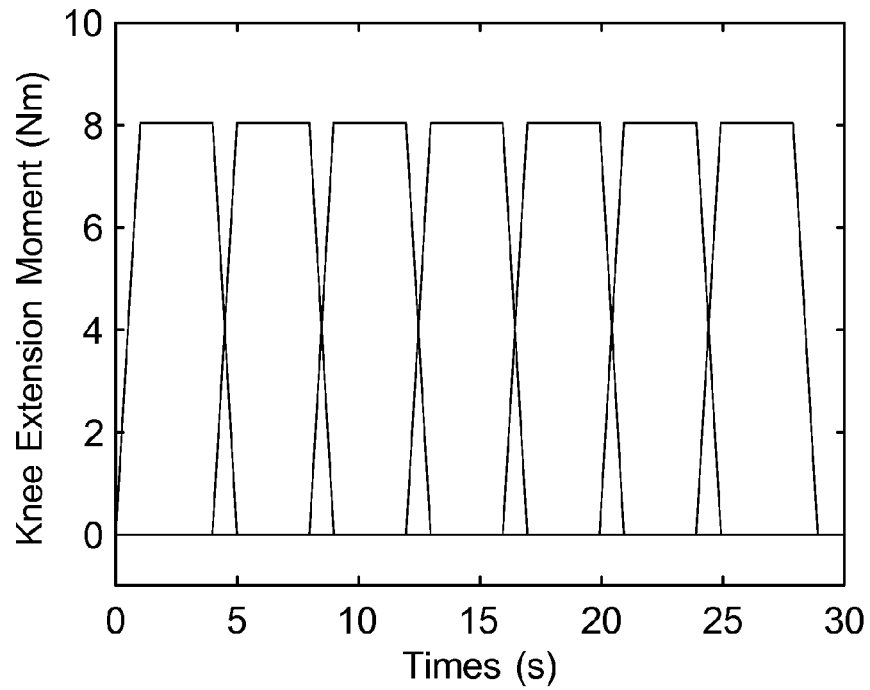
FIG. 10(a)-11 graphically depict examples of muscle stimulation paradigms.
Figure 10B:
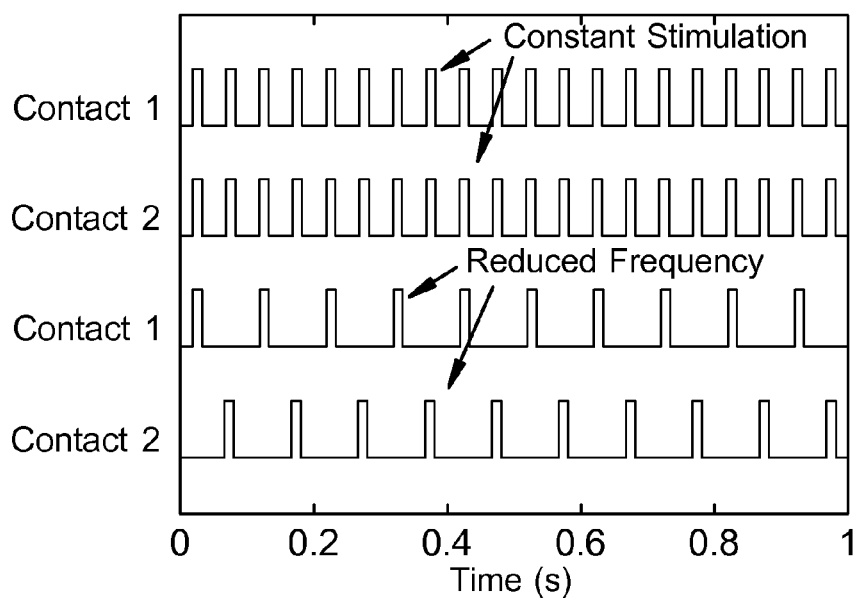
Figure 11:
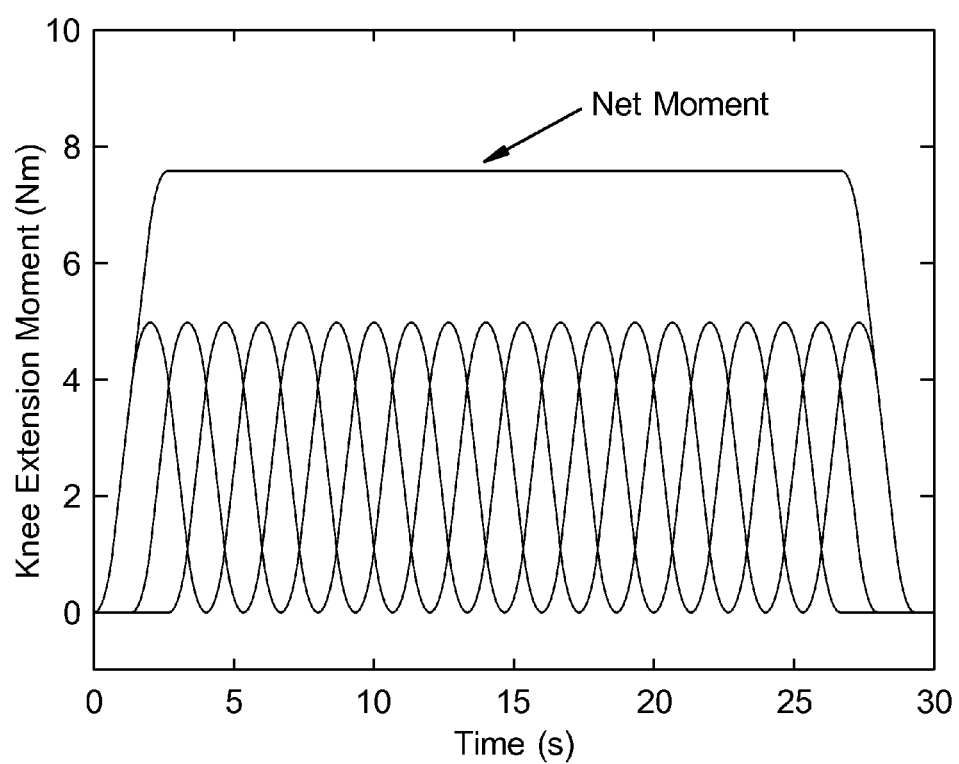

Another advanced stimulation paradigm (FIG. 10(b)), known as interleaved stimulation, has shown some promise for improving standing times in a feline model of standing with FNS. In this scheme, the overall frequency of stimulation that would normally be applied to the whole nerve is reduced for multiple independent populations of motor units by interspersing stimulus pulses, thus reducing the local stimulation frequency while maintaining the aggregate rate of activation and producing a constant muscle force or joint moment. This paradigm takes advantage of the well-established proportional relationship between stimulation frequency and the rate of muscle fatigue. By reducing frequency, the paradigm should delay the onset of fatigue, and by interspersing stimulus pulses it should reduce the ripple caused by subtetanic muscle contractions. While interleaved stimulation has shown promise in animal models, the potential for affecting the onset of fatigue in humans is still unclear.

The inventors implemented three advanced stimulation paradigms, including carousel, interleaved, and SOPS, in two individuals with SCI as part of an FNS system for standing and transfers.

Section II of the Description of Embodiments presents results from these experiments, and discusses the feasibility of implementing the paradigms, their ability to delay the onset of fatigue, and the results of attempts to extend standing time with each paradigm.

II.ii Methods

II.ii.1 Stimulation System and Subject Selection

Advanced stimulation paradigms were implemented as part of a neuroprosthesis for standing and transfers after SCI. The system 100 includes a 16-channel implanted stimulator-telemeter capable of delivering monopolar, biphasic, charge-balanced stimulus pulses with variable frequency, amplitude and pulse duration. The stimulator 110 is connected to a set of muscle-based electrodes 106 used to extend the hips and trunk, along with two self-sizing spiral nerve-cuff electrodes 106 wrapped around bilateral femoral nerves to activate the quadriceps and provide knee extension. The nerve-cuff electrodes, which have four contacts that can be controlled independently, are placed on the femoral nerve distal to branches that innervate the hip flexors rectus femoris and sartorius, but proximal to branches for the knee extensors vastus lateralis (VL), vastus medialis (VM), and vastus intermedius (VI).

This neuroprosthesis for standing and transfers was implanted in two individuals with motor complete SCI (Subject #1: level C7, ASIA B and Subject #2: level TI I, ASIA B). After implantation, each subject underwent a regimented rehabilitation and exercise program described elsewhere. This program comprised six weeks of limited mobility to ensure encapsulation of the electrodes, followed by eight weeks of exercise to build muscle strength and endurance, and approximately six months of rehabilitation and training with a physical therapist to learn to use the system. The exercise phase consisted of high force, low repetition training to build strength along with low force, high repetition training to build endurance.

II.ii.2 Selective Stimulation

The advanced stimulation paradigms described herein require control of stimulation of at least two independent agonist populations of motor units acting around a single joint. In the case of standing with the aforementioned FNS system, this means that the four contact spiral nerve-cuff electrodes must activate at least two independent populations of motor units within the knee extensor musculature. Since VL, VM, and VI all share innervations from the femoral nerve at the location of the nerve-cuff electrodes and all insert on the patellar tendon with approximately the same moment arm, for the purposes of this description, they will be treated as one large common pool of muscle fibers. Achieving selectivity of stimulation often requires striking a balance between strong muscle contractions and low overlap. Increasing the amplitude or pulse width of stimulation results in a stronger contraction but can also cause more overlap in stimulation between contacts. To reduce overlap and produce the strongest possible contractions, automated optimization of selective stimulation parameters was employed. This method, which is described in detail in Section I, takes advantage of the refractory period of motor neurons to measure overlap between pairs of contacts within an electrode. If two pulses are applied through two contacts with a short inter-contact time delay (less than 2.1 ms), any motor neurons that respond to the first pulse through the first contact will be refractory and will not respond to the second pulse through the second contact. Therefore, any deviation from the linear sum of the responses when one pulse is applied through each contact can be attributed to overlap in stimulation between the contacts.

Recruitment and pairwise overlap are quantified for all contacts within an electrode while stimulus amplitude is held constant (at 1.4 mA for Subject #1 and 0.8 mA for Subject #2) and pulse width is varied between 1 and 255 µs. By minimizing all pairwise overlaps between contacts within an electrode while simultaneously maximizing the joint moment generated by stimulating through each contact, an optimization algorithm determines the best set of parameters for selective stimulation. To account for variations in muscle strength over time, selective stimulation parameters were periodically recomputed for each contact of all electrodes using this method.

II.ii.3 Advanced Stimulation Paradigms

Three advanced stimulation paradigms—carousel, interleaved, and SOPS stimulation—were implemented in the work described in Section II. The following are brief descriptions of the paradigms and the processes for implementing them. For all paradigms, the selective stimulation parameters determined by the above optimization were treated as a ceiling, and adjustments were made between the threshold response to stimulation and those ceiling parameters to achieve desired motor output. Unless otherwise noted, stimulation was always applied at a frequency of 20 Hz. After implementation of each paradigm, constancy of joint moment was quantified by the ripple index, which is calculated by dividing the magnitude of ripples in the joint moment by the average magnitude of the joint moment.

Carousel Stimulation

Carousel stimulation (FIG. 10(a)) acts to delay the onset of fatigue by alternating stimulation between multiple selective contacts, with only one contact active at any given time. By switching stimulation between multiple independent populations of motor units, the duty cycle of stimulation is reduced by the number of contacts included in the paradigm, allowing each population to relax between contractions while maintaining a constant moment at the joint. The reduction in duty cycle and pumping action of the muscle have the potential to increase blood flow to improve oxygenation of the muscle, delay acidosis and depletion of glycogen stores, and extend the duration of contractions before the onset of fatigue.

In order to achieve a smooth, constant joint moment, it is important that the muscle forces generated by all independent populations are equal. This was achieved by recording isometric joint moment in response to trains of stimuli through each contact and manually adjusting stimulus pulse width to achieve equal joint moments through all contacts. In practice, this means that the joint moment generated by each contact was limited to that generated by the weakest contact. To further ensure ripple-free contractions, the relationship between the ripple index and the period of cycling between contacts was quantified for periods of 2 and 10 seconds. For ease of implementation and to minimize ripple, no ramp was used when switching stimulation between contacts.

Interleaved Stimulation

Interleaved stimulation (FIG. 10(b)) relies on the relationship between the rate of fatigue and the frequency of stimulation to delay the onset of fatigue. High frequency stimulation is associated with depletion of and reduced sensitivity to $Ca^{2+}$ within the muscle, so stimulation at lower frequencies may delay the onset of fatigue. However, if stimulation frequency is too low there is also the potential to cause low frequency fatigue, a phenomenon marked by long-term fatigue, often lasting 24 hours or more, as a result of impairment of excitation-contraction coupling in the muscle. Additionally, while reducing stimulation frequency may reduce the effects of high frequency fatigue and prolong muscle contractions, it can also cause contractions to be subtetanic with ripple in the resultant joint moment. While any single population of motor units may not achieve a fused contraction, by including different time delays for each contact within an electrode, the paradigm is designed to allow those ripples to sum to produce a constant joint moment while also reducing the effects of fatigue. Here, the ripple index was measured for stimulation frequencies of 10 and 12 Hz to determine the best frequency to generate smooth contractions. Stimulus pulse width was maintained at the maximal levels determined by optimization of selectivity, as these would provide the strongest possible contractions without overlap.

Sum of Phase-Shifted Sinusoids Stimulation

The SOPS stimulation paradigm (FIG. 11) relies on the same principles as three-phase power generation to produce a constant motor output. In the SOPS paradigm, the modulation of stimulation pulse width causes the joint moments generated by multiple independent motor unit populations to oscillate with equal amplitude and frequency, but offset phase, so that their combined output is a constant value equal to the sum of their average joint moments. For electrodes that can stimulate more than two independent populations of motor units, total joint moment produced with the SOPS paradigm will, by definition, be greater than the contribution of any single independent population of motor units. This allows a reduction in duty cycle as compared to constant stimulation, but a higher total joint moment than carousel stimulation, which is only as strong as the weakest population of motor units.

The duty cycle of SOPS stimulation is higher than that of carousel stimulation, although it may have a similar effect on improvement in circulation and oxygenation of the tissue, reduction of acidosis, delay in depletion of glycogen and ATP stores within the muscle, and subsequent delay in the onset of fatigue.

In order to achieve sinusoidal oscillations in joint moment, for each contact within the nerve-cuff a pulse-width modulated isometric tetanic recruitment curve was used as a transfer function between the desired joint moment and an estimate of the stimulation pattern required to generate it. The recruitment curve was created by applying three second trains of stimulus pulses through each contact of the nerve cuff with pulse widths ranging from 1 to 255 µs while the knee was held in 20° of flexion by a dynamometer which measured knee extension moment. As with carousel stimulation, the SOPS paradigm will only achieve ripple-free joint moment if the maximum joint moments generated by stimulating through all contacts are equal. Therefore, the same stimulation parameters used during carousel stimulation were used here as the maxima of sinusoidal oscillations. The relationship between ripple and oscillation period was determined by measuring the ripple index for oscillation periods of 2 and 10 seconds.

II.ii.4 Fatigue Testing

To determine the effect on fatigue of each paradigm, isometric fatigue tests were performed while knee extension moment was recorded and stimulation was applied through each nerve-cuff electrode using one of the three advanced paradigms or constant stimulation. During each test, which lasted 30 minutes, the knee was held in 20° of flexion with the knee joint center aligned with one axis of a 6 degree-of-freedom load cell attached to a robotic dynamometer. Data were low-pass filtered at 31.25 Hz and sampled at 150 Hz. Fatigue tests were separated in time by a minimum of 6 hours. $T_{50}$, a commonly used fatigue metric in which elapsed time before knee moment reached 50% of the initial value, was measured for each paradigm. Also, based on previous biomechanical modeling work demonstrating that 0.135 Nm of knee extension moment per kg of body weight is required to keep each knee locked during standing, the elasped time to reach that value ($T_{0.135}$) was also calculated as an estimate of potential standing duration. A one-way ANOVA was used to compare fatigue results across paradigms.

II.ii.5 Maximum Standing Time

While fatigue tests are a useful way to measure the rate of fatigue while avoiding the biomechanical variability inherent to standing, it is important to determine the functional impact of each paradigm on standing. To accomplish this, maximum standing time before fatigue was measured with each paradigm and constant stimulation while each subject stood on a set of force plates with hands on a set of instrumented parallel bars to measure the distribution of weight through the arms and legs. Before each test, the subject was instructed to stand for as long as possible, and the test continued until either the subject requested to sit, a physical therapist noticed knee buckling, or one hour elapsed. Maximum standing time tests were separated by a minimum of 6 hours.

II.iii Results

II.iii.1 Selective Stimulation

Figure 12:
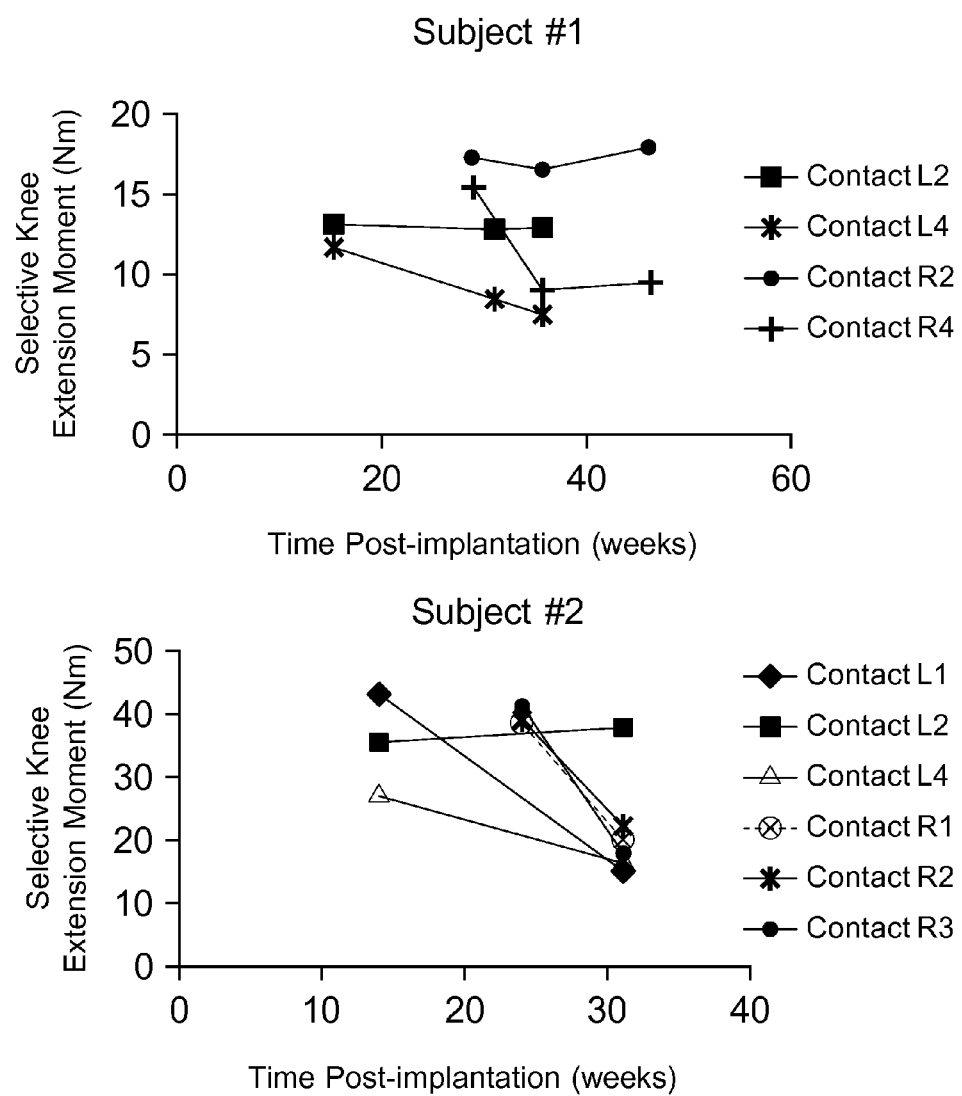

The results of optimization of selective stimulation parameters are discussed in detail in Section I. Shown in FIG. 12 are the moments as a result of stimulus parameters as determined by the optimization method. Data are shown for time points after implantation at which advanced stimulation paradigms were implemented and fatigue tests were performed. For Subject #1, optimization could achieve two contacts within each nerve-cuff electrode that could generate at least 7.5 Nm of knee extension moment with less than 10% overlap between contacts. For Subject #2, optimization could achieve three contacts within each nerve-cuff electrode that could generate at least 15 Nm of knee extension moment with less than 10% overlap between pairs of contacts. It should be noted that Subject #2 suffered a left femur fracture unrelated to the implanted FNS system at 14.7 weeks after implantation, just after the first set of data points shown in FIG. 12. This fracture caused significant disuse of the system, and may have led to changes in strength and optimal stimulation parameters.

II.ii.2 Advanced Stimulation Paradigms

Carousel Stimulation

Figure 13:
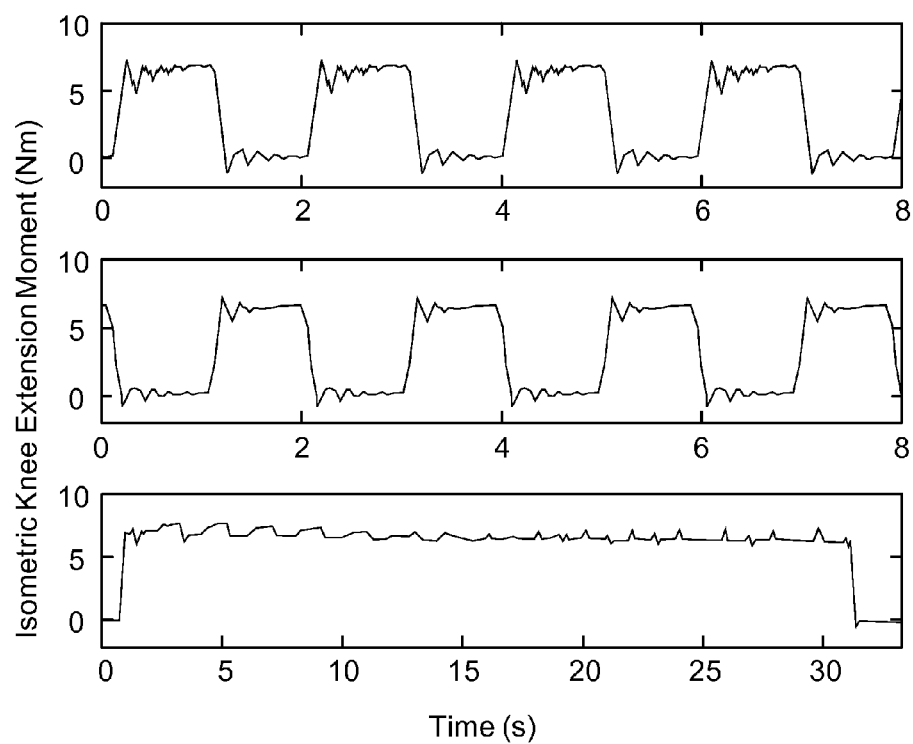
Figure 14:
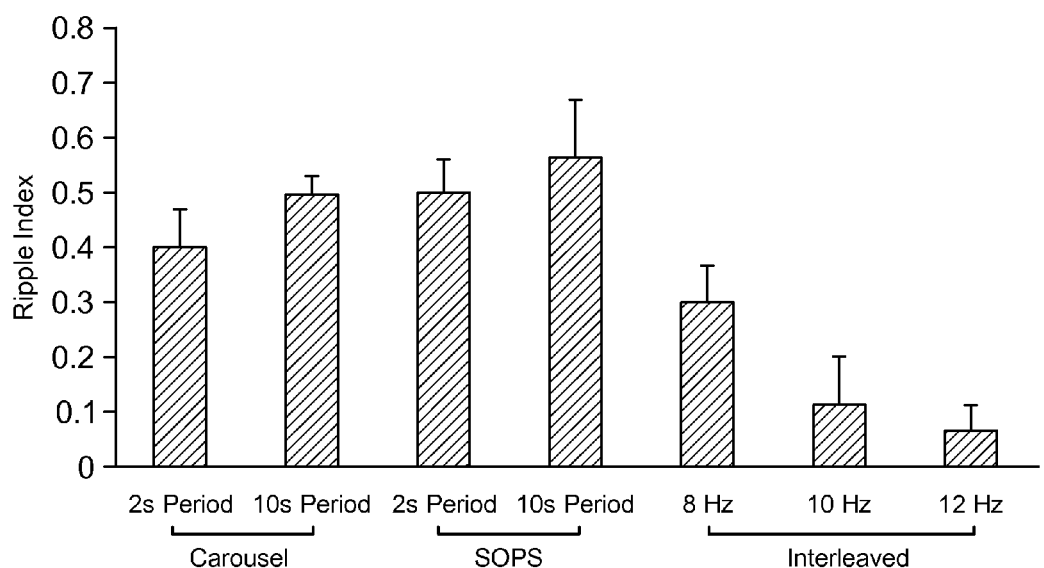

Shown in FIG. 13 are examples of isometric knee extension moment recorded during stimulation through two contacts separately and during carousel stimulation. Shown in FIG. 14 are measurements of average ripple index for 2 and 10 second oscillation periods. Ripple was lower and contractions were smoother with a 2 second oscillation period, which was used during all subsequent fatigue and maximum standing time tests.

Interleaved Stimulation

Figure 15:
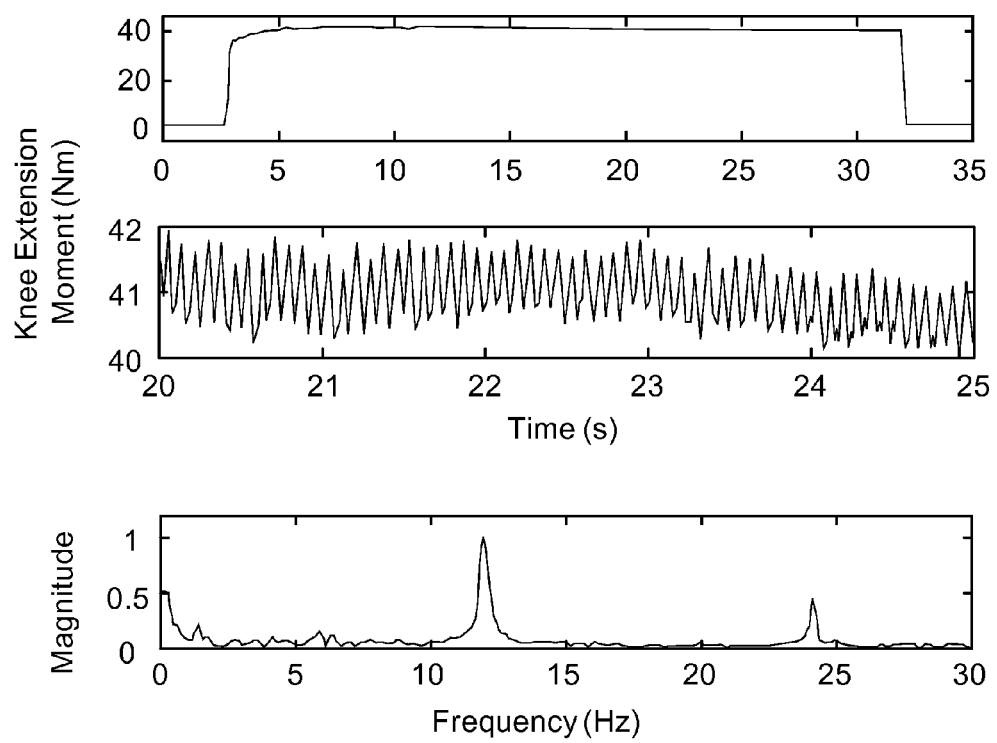

Shown in FIG. 15 is an example of isometric knee extension moment recorded during interleaved stimulation of three contacts, each stimulated at a frequency of 12 Hz, along with an expanded version of 5 seconds of the same recording. During interleaved stimulation, frequency was held at 12 Hz as this achieved the lowest ripple (FIG. 14). Also shown in FIG. 14 is a plot of frequency spectrum of the expanded 5 second recording, with peaks at 12 and 24 Hz corresponding to ripple in the recorded signal.

Sum of Phase-Shifted Sinusoids Stimulation

Figure 16:
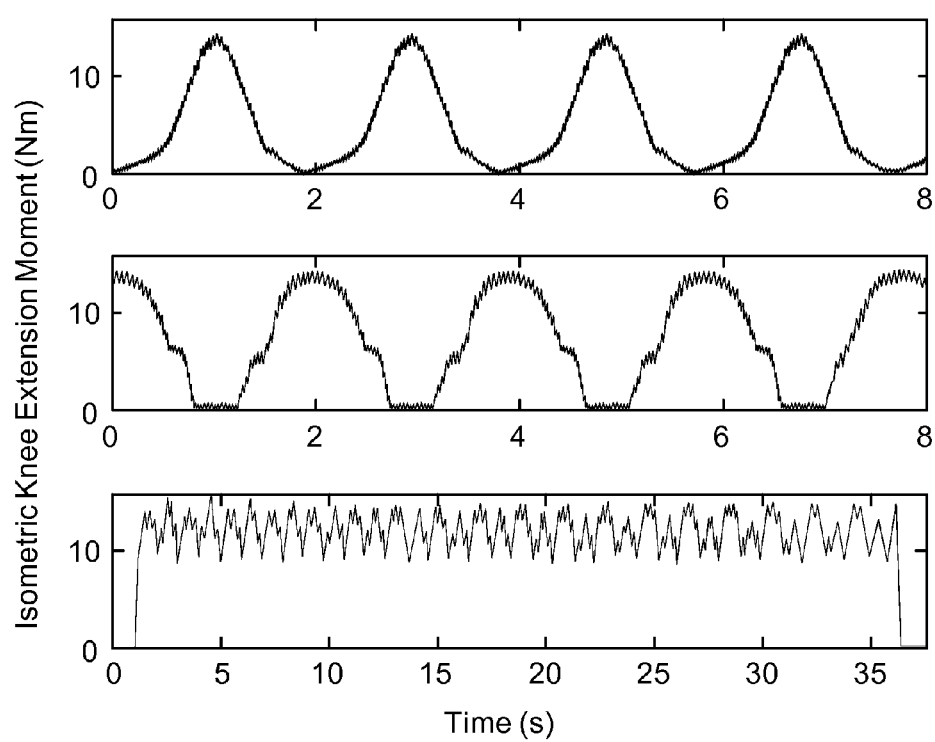
Figure 17A:
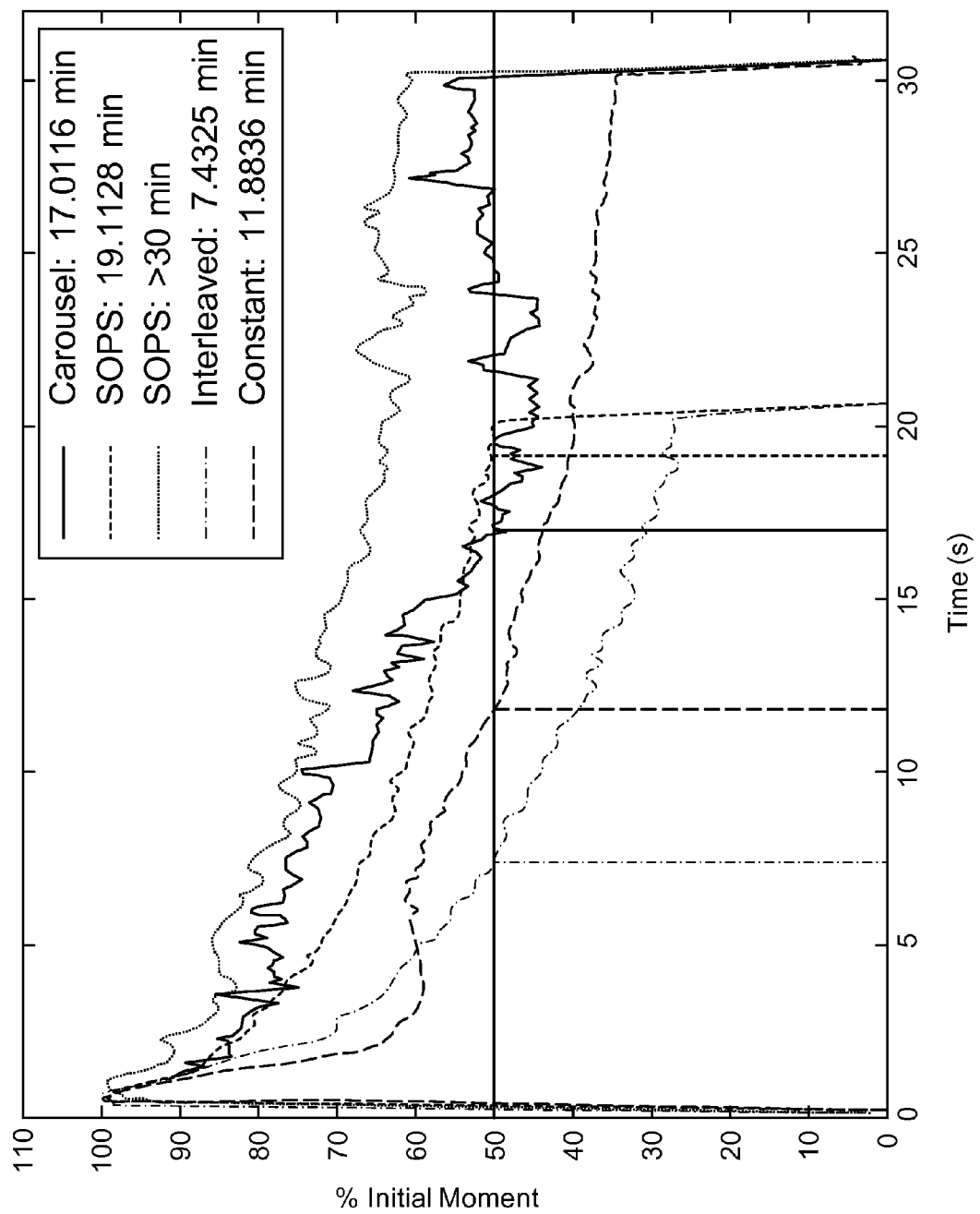
Figure 17B:
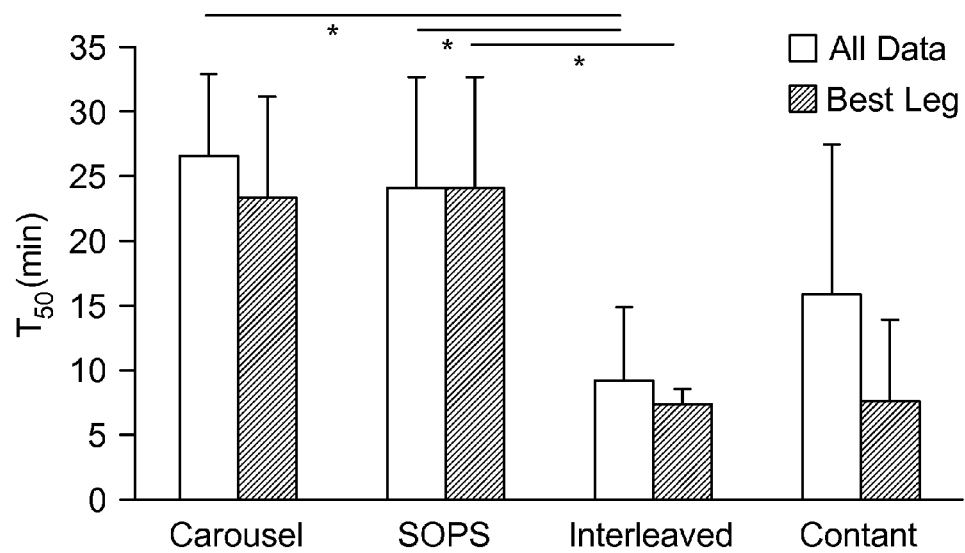

Shown in FIG. 16 are examples of isometric knee extension moment recorded during stimulation through two contacts separately and during SOPS stimulation. While the individual signals resemble sinusoids, they are clearly not a perfect representation of sinusoidal oscillation, and cause ripple when summed together during SOPS stimulation. As shown in FIG. 14, an oscillation period of 2 seconds had a lower ripple index than an oscillation period of 10 seconds. Therefore, 2 second oscillations were used in all subsequent fatigue and maximum standing time tests.

II.iii.3 Fatigue Testing

Fatigue tests were performed with both subjects, using each of the advanced stimulation paradigms along with constant stimulation. Shown in FIG. 17(*a*) are examples of isometric knee extension moment recordings during fatigue tests on the right leg of Subject #1. These traces are filtered with a 1000 point moving-average and normalized by the maximum response. $T_{50}$, which occurs when each trace crosses the horizontal black line, can be seen in the plot. Shown in FIG. 17(*b*) are mean $T_{50}$ data for all paradigms across bothsubjects, as well as for the best leg for each subject. Analysis including only the best leg was performed because the left leg for Subject #1 was too weak to lock during standing with carousel and SOPS stimulation and the right leg for Subject #2 was highly spastic, making knee extension moment data exceedingly noisy. Based on a one-way ANOVA, there was a statistically significant difference in $T_{50}$ for both carousel and SOPS as compared to interleaved stimulation, but no difference between any advanced paradigm and constant stimulation.

Figure 18A:
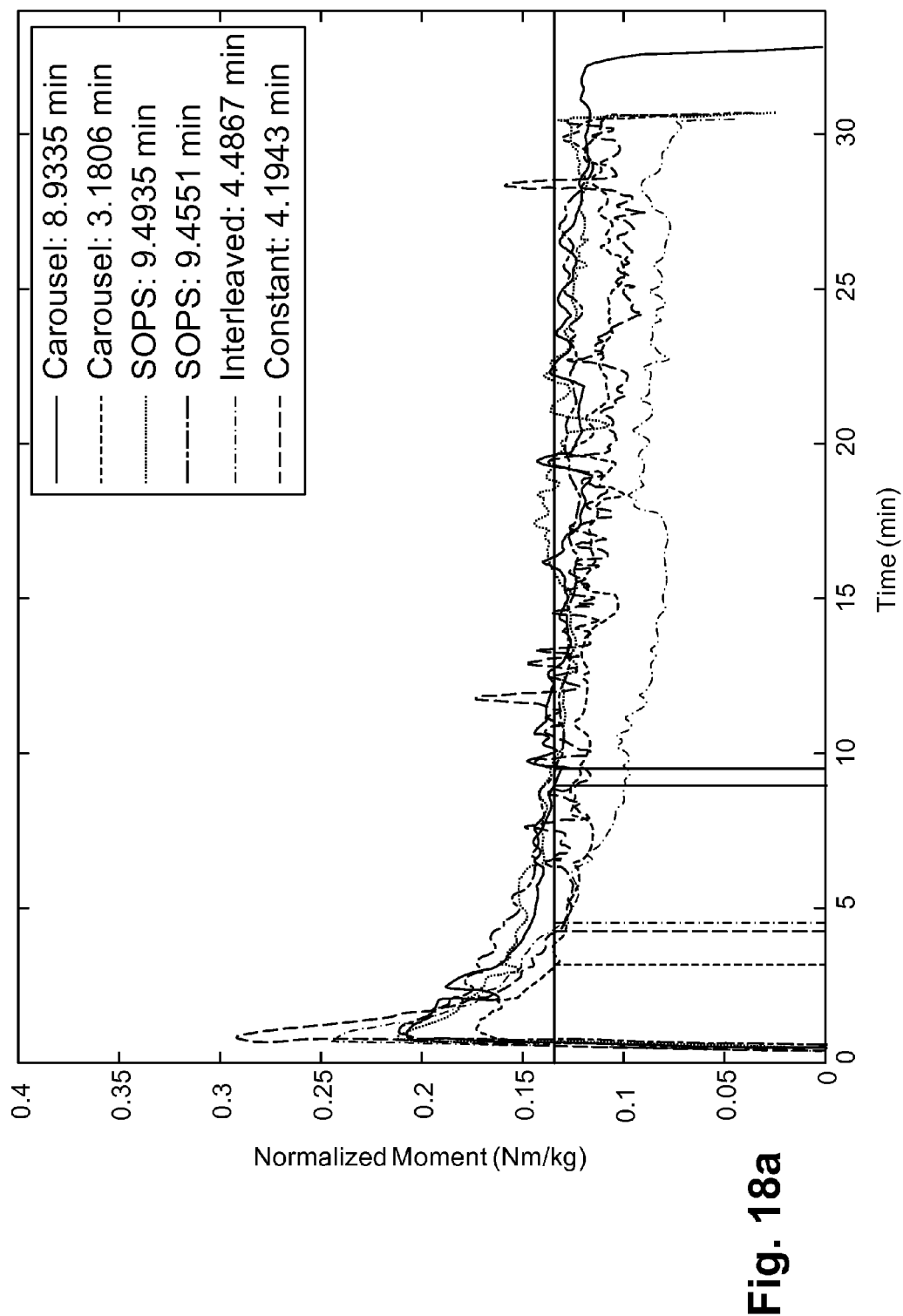
Figure 18B:
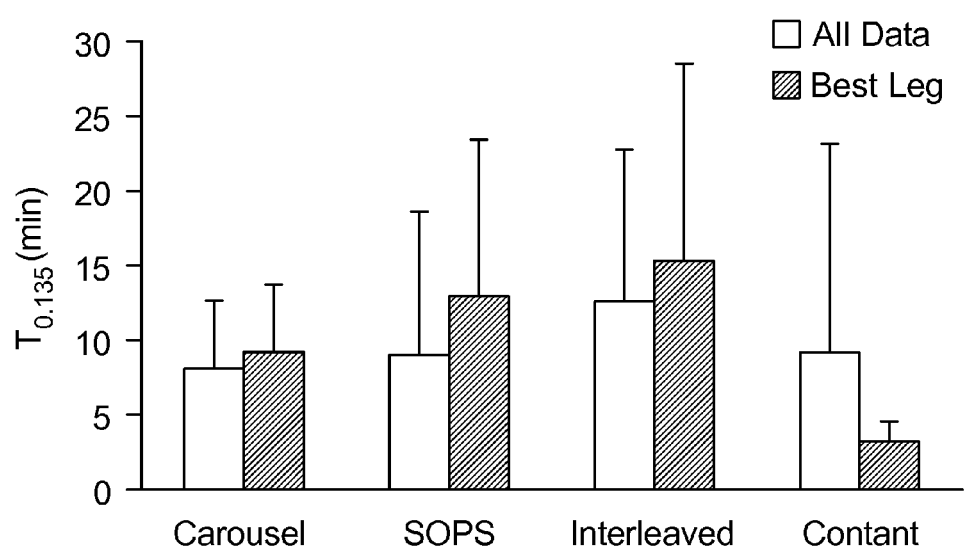

Shown in FIG. 18(*a*) are examples of isometric knee extension moment recordings during fatigue tests on the left leg of Subject #1. These traces are filtered with a 1000 point moving-average and normalized by the subject's body weight. $T_{0.35}$, which occurs when each trace crosses the horizontal black line, can be seen in the plot. Shown in FIG. 18(*b*) are mean $T_{0.135}$ data for all paradigms across both subjects, as well as for the best leg for each subject. As with $T_{50}$, analysis was also performed over data for the best leg of each participant. Based on a one-way ANOVA, there were no statistically significant differences in $T_{0.135}$ for any advanced paradigm or constant stimulation.

It should be noted that, because of time constraints, fatigue tests could not be performed with all paradigms on consecutive days soon after optimization of selective stimulation parameters. Instead, after optimization of stimulation parameters, a subset of paradigms (e.g., carousel, SOPS, and interleaved) were used in testing on consecutive days, and then, months later, after repeated optimization of stimulation parameters, a different subset of paradigms (e.g., carousel, SOPS, and constant) were used in testing. This means that strength and selective stimulation parameters may have changed between comparisons of some stimulation paradigms. It should also be noted that there is a ceiling effect in both $T_{50}$ and $T_{0.135}$ data because, in some cases, knee extension moment had still not dropped below 50% of maximum or 0.135×body weight after 30 minutes. In these cases, for the purpose of calculating averages and standard deviations, $T_{50}$ and $T_{0.135}$ were treated as 30 minutes.

II.iii.4 Maximum Standing Time

Maximum standing time tests were performed with both subjects using all fatigue delaying stimulation paradigms. Because of the relatively weak joint moments achieved with selective stimulation, it was not possible to achieve long-duration standing with Subject #1 while using any of the advanced stimulation paradigms. For each paradigm, a physical therapist reported knee bending shortly after the sit-to-stand transition was achieved, so the subject never stood for more than one minute with any advanced stimulation paradigm. Standing was also attempted with Subject #1 using stimulation parameters than included up to 30% overlap, but even under those conditions, muscle contractions were not strong enough to keep the knees locked during standing with selective stimulation. It should be noted that the subject can stand using constant stimulation, but with stimulus pulse widths that are longer than those that achieve selective stimulation and likely cause significant overlap in stimulation.

Figure 19:
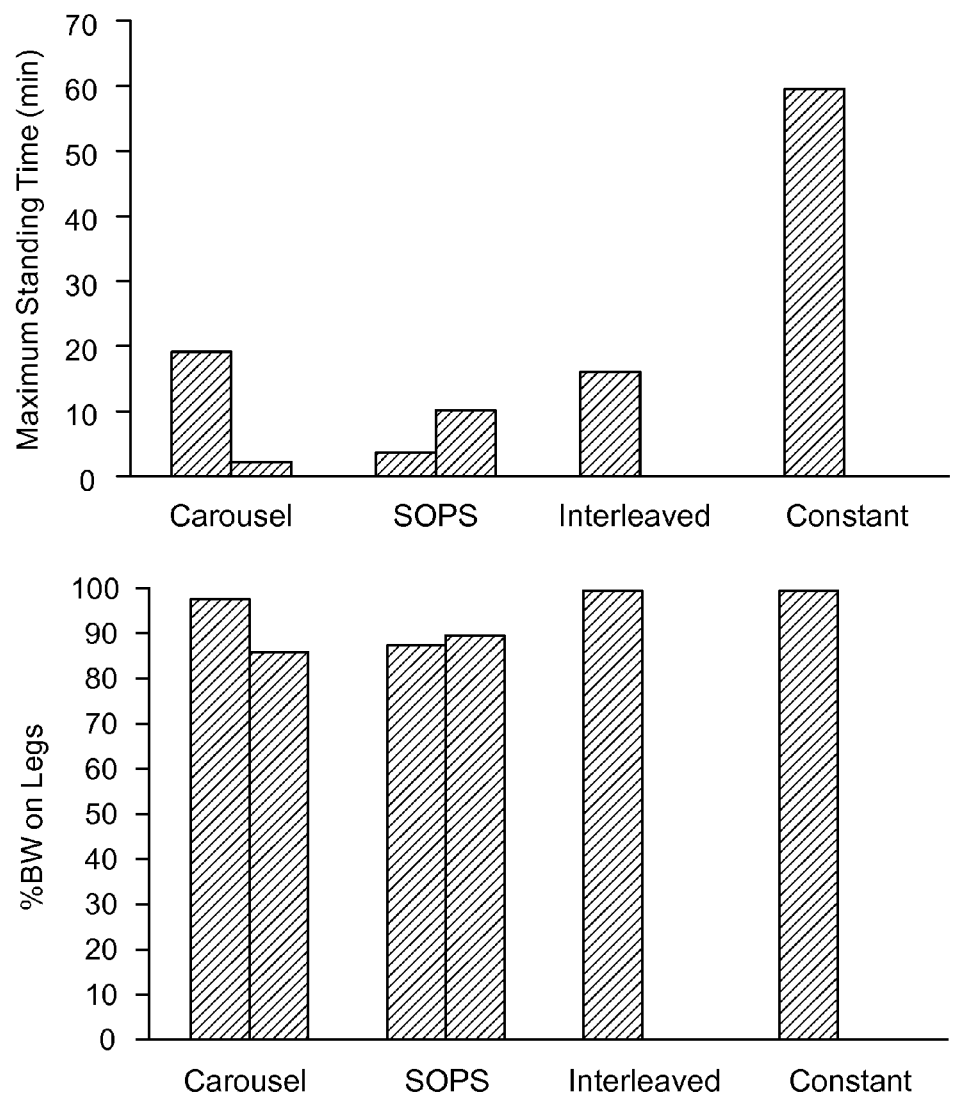

Subject #2 had significantly stronger selective knee extension moments than Subject #1 and could successfully stand with each of the paradigms, although a physical therapist did notice some knee-bending in the weaker left leg. To attempt to avoid this bending, stimulation parameters were chosen that included up to 25% overlap between pairs of contacts, but resulted in significantly stronger knee extension moments. Because of time constraints, maximum standing time tests were repeated twice for carousel and SOPS stimulation, but only performed once for interleaved and constant stimulation. Shown in FIG. 19 are maximum standing times achieved for each stimulation paradigm, along with steady state % BW supported on the legs. The subject stood for at least 10 minutes and could support at least 85% BW on his legs with each paradigm, although, during repeated trials he also experienced standing times less than 5 minutes with carousel and SOPS stimulation. With constant stimulation, the subject stood for one hour before the trial ended.

II.iv Discussion

The data presented in Section II demonstrate the feasibility of implementing advanced stimulation paradigms in humans, and that it is possible to use those paradigms to lock the knees during standing. In each subject, it was possible to achieve contractions with the patterns necessary to implement carousel and SOPS stimulation, and to produce less than 10% ripple with interleaved stimulation. Subjects reported that the ripple they experienced was not too excessive to tolerate, although anecdotally they did prefer the low frequency ripple that occurred with carousel and SOPS stimulation to the higher 12 Hz vibrations with interleaved stimulation. Subject #2, who has some spared sensation, reported enjoying the feeling of cyclic contractions in the quadriceps during SOPS stimulation.

While these results provide evidence that it is possible to implement these stimulation paradigms in humans, it is less clear whether the paradigms can delay the onset of fatigue.

There were no statistically significant differences in either $T_{50}$ or $T_{0.135}$ for any advanced stimulation paradigm as compared to constant stimulation. There does appear to be a trend in increased time before fatigue, especially if only the best leg for each subject is included in analysis, but with such a small sample set, it is not possible to make any conclusions about the significance of that trend, Similarly, when maximum standing time is compared for each stimulation paradigm, there is no clear evidence that any paradigm delays fatigue more than constant stimulation, In fact, Subject #2 was able to stand between three and six times longer with constant stimulation than with any other paradigm during these tests.

It is important to note that, even though it is unclear what effect these paradigms have on delaying fatigue, Subject #2 was able to stand for at least 10 minutes with each paradigm, demonstrating that it is possible to use them to lock the knees for significant periods of time. On the other hand, because the selective response to stimulation was significantly weaker in Subject #1, it was not possible to achieve standing times longer than one minute with any of the advanced stimulation paradigms, even if 30% overlap was allowed between contacts. This result suggests that it is important to consider the implementation of these paradigms on a case-by-case basis with each user of FNS systems. In some subjects and in some applications, it may not be possible to implement all paradigms, or it may make more sense to implement one paradigm over another for a given application.

The advanced stimulation paradigms presented here are designed to affect specific physiological processes in order to delay the onset of fatigue. Carousel and SOPS stimulation reduce the duty cycle of stimulation with the goal of improving blood flow and oxygenation of muscle tissue while reducing lactic acid build-up. Interleaved stimulation is designed to reduce the frequency of stimulation to prevent depletion of $Ca^{2+}$ stores, while also attempting to avoid the long-duration effects of low frequency fatigue. When comparing between stimulation paradigms, while there was no statistical difference in $T_{0.135}$ or maximum standing time, $T_{50}$ was statistically larger for carousel and SOPS stimulation than for interleaved stimulation, suggesting either that it was not possible to avoid low frequency fatigue with interleaved stimulation or that paradigms that affect blood flow to the muscle tissue may have a larger effect on fatigue than those that reduce the frequency of stimulation. While interleaved stimulation acts to restore the concentration of $Ca^{2+}$ stores in the sarcoplasmic reticulum of the muscle by allowing for more time between stimulus pulses, a similar effect likely occurs in carousel and SOPS stimulation during the rest phases in between tetanic contractions. This suggests that the key to delaying fatigue may be in providing the best possible blood flow to the tissue, allowing for increased oxygenation, reduced lactic acid build-up, and maintenance of glycogen and ATP stores in the muscle.

II.v Conclusions

Section II presents the results of first-in-man implementations of carousel, interleaved, and SOPS stimulation paradigms to delay the onset of fatigue in a motor systems neuroprosthesis. It was demonstrated that it is possible to achieve the patterns of activation necessary to implement each paradigm, and that contractions with tolerable amounts of ripple could be achieved by simple ad hoc tuning of stimulation parameters. In one subject, knee joint moments during all advanced stimulation paradigms were sufficiently large to allow for at least 10 minutes of standing without knee buckling, but in another subject, joint moments were only sufficient for short duration (<1 min) standing. While there appear to be trends towards improved fatigue delay in measures such as $T_{50}$ and $T_{0.135}$, no statistical conclusions could be made about the ability of any advanced stimulation paradigm to extend standing time as compared to constant stimulation. [end of Section II]

With reference back to FIG. 1, then, it can be seen that the SOPS paradigm can be used with the system 100 to provide desired motor unit stimulation via any suitable FNS system, having any desired type and number of electrodes 106. For example, as previously mentioned, the stimulator assembly 110 can be configured to provide a time-varying electrical current to each electrode 106 of the plurality of electrodes. The time-varying current can be provided such that a sum of time-varying moments induced across all of the plurality of motor units remains substantially constant and non-zero. Optionally, the stimulator assembly 110 may be configured to provide a time-varying current such that each time-varying moment varies sinusoidally at a common frequency. The stimulator assembly 110 can be configured to determine appropriate stimulation currents for the plurality of electrodes to provide the time-varying moment at their respective motor units according to a model representing recruitment and overlap characteristics of the plurality of electrodes and the plurality of motor units.

Optionally, a peak moment associated with the time-varying moment induced at each of the plurality of motor units may be less than the non-zero sum, such as being less than three-quarters of the non-zero sum.

Also as previously mentioned, the plurality of electrodes 106 may comprise N electrodes, where N is a positive integer greater than two, including a first electrode 106. In such case, the sinusoidally-varying moment induced by a second electrode 106 of the N electrodes may be shifted in phase relative to the sinusoidally-varying moment induced by the first electrode by 2*pi/N radians. For example, the plurality of electrodes 106 may comprise three electrodes, such that the sinusoidally-varying moment induced by the second electrode of the three electrodes is shifted in phase relative to the sinusoidally-varying moment induced by the first electrode by 2*pi/3 radians, and the sinusoidally-varying moment induced by a third electrode of the three electrodes is shifted in phase relative to the sinusoidally-varying moment induced by the first electrode by 4*pi/3 radians. Stated more generally, the sinusoidally-varying moment induced by an $i^{th}$ electrode of the plurality of electrodes in its associated motor unit may have a phase shift of 2i*pi/N radians relative to the sinusoidally-varying moment induced by a first electrode of the plurality of electrodes. That sinusoidally-varying moment can be induced at a same amplitude for any number N of independent motor units, such that a sum of the moment provided across all of the N motor units is substantially constant and non-zero. In this manner, the SOPS paradigm illustrated in FIG. 11 and the associated text above can be provided to one or more motor units as desired.

The SOPS advanced stimulation paradigm takes advantage of the mathematical relationship that the sum of multiple sinusoids with equal frequency and amplitude and evenly distributed phase will be constant. Below is the mathematical derivation of an example of this relationship for three independent motor units or populations of motor units, but a similar approach could be taken to any number of independent populations (greater than 1).

First, define three isometric joint moments with oscillating magnitude, constant moment arm, and equally distributed phase:

$$M_A = r_A(\alpha_A \sin(\pi t) + \alpha_A) \quad \text{(Eq. 5)}$$

$$M_B = r_B(\alpha_B \sin(\pi t) + 2/3\pi) + \alpha_B \quad \text{(Eq. 6)}$$

$$M_C = r_C(\alpha_C \sin(\pi t) + 4/3\pi) + \alpha_C \quad \text{(Eq. 7)}$$

where $M_n$ is the joint moment produced by contact n, $r_n$ is the moment arm for motor units activated by contact n, $a_n$ is the amplitude of the peak force generated by contact n, and $\alpha_n$ is the offset of the oscillations of contact n.

If all moments are agonists, and all moment arms are equal (as is the case with the vasti at the knee) then we have:

$$M_{total} = M_A + M_B + M_C \quad \text{(Eq. 8)}$$
$$= r(\alpha_A \sin(\pi t) + \alpha_A + \alpha_B \sin(\pi t + 2/3\pi) +$$
$$\alpha_B + (\alpha_C \sin(\pi t) + 4/3\pi) + \alpha_C)$$

Using the trigonometric identity $$\sin(m+n) = \sin(m)\cos(n) + \cos(m)\sin(n) \quad \text{(Eq. 9)}$$

we now have:

$$M_{total} = \quad \text{(Eq. 10)}$$
$$r(\alpha_A \sin(\pi t) + \alpha_A + \alpha_B(\sin(\pi t)\cos(2/3\pi) + \cos(\pi t)\sin(2/3\pi)) +$$
$$\alpha_B + \alpha_C(\sin(\pi t)\cos(4/3\pi) + \cos(\pi t)\sin(4/3\pi)) + \alpha_C)$$

which can be simplified to $$M_{total} = r(\alpha_A \sin(\pi \tau) + \alpha_a) + \alpha_B\left(1/2 \sin(\pi \tau) + \sqrt{3}/2 \cos(\pi t)\right) + \quad \text{(Eq. 11)}$$
$$\alpha_B - \alpha_C\left(1/2 \sin(\pi t) + \sqrt{3}/2 \cos(\pi t)\right) + \alpha_C$$

Now, if $\alpha_A = \alpha_B = \alpha_C$, then the $\sin(\pi t)$ terms and the $\cos(\pi t)$ terms cancel out, leaving $$M_{total} = r(\alpha_A + \alpha_B + \alpha_C) \quad \text{(Eq. 12)}$$

In order to provide a method for stimulating a plurality of independent, mutually agonist motor units with the SOPS paradigm, the user can provide a first stimulation current to an electrode associated with a first motor unit of the plurality of motor units to induce a first sinusoidally-varying moment, having a first frequency, in the first motor unit. A second stimulation current is provided to an electrode associated with a second motor unit of the plurality of motor units to induce a second sinusoidally-varying moment, having the first frequency, in the second motor unit with a phase shift, relative to the first sinusoidally-varying moment, of 2*pi/3 radians. A third stimulation current is provided to an electrode associated with a third motor unit of the plurality of motor units to induce a third sinusoidally-varying moment, having the first frequency, in the third motor unit with a phase shift, relative to the first sinusoidally-varying moment, of 4*pi/3 radians. In one implementation, all of the first, second, and third sinusoidally-varying moments have a same amplitude, such that a sum of the moments provided across all of the plurality of motor units is substantially constant and non-zero. In accordance with an aspect of the invention, appropriate first, second, and third stimulation currents can be determined according to a model representing recruitment and overlap characteristics of first, second, and third motor units and their associated electrodes.

While aspects of the present invention have been particularly shown and described with reference to the preferred embodiment above, it will be understood by those of ordinary skill in the art that various additional embodiments may be contemplated without departing from the spirit and scope of the present invention. For example, the specific methods described above for using the system 100 are merely illustrative; one of ordinary skill in the art could readily determine any number of tools, sequences of steps, or other means/options for placing the above-described apparatus, or components thereof, into positions substantively similar to those shown and described herein. Any of the described structures and components could be integrally formed as a single unitary or monolithic piece or made up of separate sub-components, with either of these formations involving any suitable stock or bespoke components and/or any suitable material or combinations of materials such as, but not limited to, stainless steel, titanium, platinum, Nitinol, epoxies, urethanes, metals, polymers, ceramics, and the like; however, the chosen material(s) should be biocompatible for many applications of the present invention. Nerves, muscles, fascicles, and/or any other stimulated structures of the living body are described herein without restriction as "motor units", due to the integrated and connected nature of all of these structures with respect to the described use environments. Though certain components described herein are shown as having specific geometric shapes, all structures of the present invention may have any suitable shapes, sizes, configurations, relative relationships, cross-sectional areas, or any other physical characteristics as desirable for a particular application of the present invention. Any structures or features described with reference to one embodiment or configuration of the present invention could be provided, singly or in combination with other structures or features, to any other embodiment or configuration, as it would be impractical to describe each of the embodiments and configurations discussed herein as having all of the options discussed with respect to all of the other embodiments and configurations. Other electrode designs and stimulation paradigms could be provided, such as, but not limited to, field steering, bipolar or tripolar electrode configurations, and/or different geometries such as a flat cuff cross-section to further improve selectivity and performance. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, we claim:

1. A system comprising:
   an implantable electrode, comprising a number (N) of independently-controlled contacts configured to be arranged so that each contact stimulates a respective nerve of a motor unit, wherein N is a positive integer greater than two; and
   a stimulator assembly configured to provide a stimulation current, comprising N waveforms, each varying sinusoidally at a common frequency and shifted in phase by $2\pi/N$ relative to the other waveforms, to the electrode, wherein the N waveforms are provided to the N contacts over time to intermittently activate one or more motor units to ensure that a sum of respective responses of muscle fibers of the motor units remains substantially constant and non-zero without diminishing the responses.

2. The system of claim 1, wherein the electrode comprises three contacts (N=3) and the phase shift between stimulation currents delivered to each contact is (2pi)/3 radians.

3. The system of claim 1, wherein the stimulator assembly is configured to determine appropriate stimulation currents for the N contacts according to a model representing recruitment and overlap characteristics of the nerves associated with the motor units.

4. The system of claim 1, wherein a peak output associated with the responses of the muscle fibers of the motor units is less than the non-zero sum.

5. The system of claim 4, wherein the peak output associated with the responses of the muscle fibers of the motor units is less than three-quarters of the non-zero sum.

6. The system of claim 1, wherein the stimulator assembly is configured to be implanted within the living body.

7. The system of claim 6, further comprising a system control configured to communicate with the stimulator assembly and the electrode contacts to adjust the frequency, amplitude, and pulse duration associated with the stimulation current.

8. A system comprising:
   an implantable electrode, comprising N electrode contacts, where N is a positive integer greater than two, each configured to be arranged so that each electrode contact activates a nerve of a motor unit; and
   a stimulator assembly configured to provide a set of N electrical waveforms, each varying sinusoidally at a common frequency and shifted in phase by $2\pi/N$ relative to the other electrical waveforms, to the N electrode contacts to activate at least two nerves of at least two motor units intermittently, wherein the set of electrical waveforms is configured based on a stimulation parameter determined based on a maximization of a desired response associated with muscle fibers of the motor units and a minimization of an overlap between the N contacts.

9. The system of claim 8, wherein N is equal to three.

10. The system of claim 8, wherein the stimulator assembly is configured to be implantable within a living body.

11. The system of claim 10, further comprising a system control configured to communicate with the stimulator to adjust one of a stimulus amplitude, a pulse duration, and a frequency of the set of electrical waveforms.

* * * * *

UNITED STATES PATENT AND TRADEMARK OFFICE
CERTIFICATE OF CORRECTION

PATENT NO. : 9,468,753 B2
APPLICATION NO. : 13/918440
DATED : October 18, 2016
INVENTOR(S) : Lee Fisher et al.

Page 1 of 1

It is certified that error appears in the above-identified patent and that said Letters Patent is hereby corrected as shown below:

In the Specification

In Column 1, after Line 10 insert:
--GOVERNMENT FUNDING
This work was supported, at least in part, by grant number EB001889 from The National Institutes of Health. The United States government has certain rights in this invention.--

Signed and Sealed this
Second Day of January, 2018

Joseph Matal
*Performing the Functions and Duties of the
Under Secretary of Commerce for Intellectual Property and
Director of the United States Patent and Trademark Office*

UNITED STATES PATENT AND TRADEMARK OFFICE
CERTIFICATE OF CORRECTION

PATENT NO. : 9,468,753 B2
APPLICATION NO. : 13/918440
DATED : October 18, 2016
INVENTOR(S) : Lee Fisher et al.

Page 1 of 1

It is certified that error appears in the above-identified patent and that said Letters Patent is hereby corrected as shown below:

In the Specification

Column 1, Line 10 before the heading TECHNICAL FIELD add the following:
--GOVERNMENT FUNDING
This invention was made with government support under EB001889 awarded by the National Institutes of Health. The government has certain rights in the invention.--

This certificate supersedes the Certificate of Correction issued January 2, 2018.

Signed and Sealed this
Twenty-ninth Day of July, 2025

Coke Morgan Stewart
*Acting Director of the United States Patent and Trademark Office*